US009428738B2

(12) United States Patent
Menéndez Arias et al.

(10) Patent No.: US 9,428,738 B2
(45) Date of Patent: Aug. 30, 2016

(54) HIV TYPE 1 GROUP O REVERSE TRANSCRIPTASES THAT ARE ACTIVE AT HIGH TEMPERATURES

(71) Applicant: CONSEJO SUPERIOR DE INVESTIGACIONES CIENTÍFICAS (CSIC), Madrid (ES)

(72) Inventors: Luis Menéndez Arias, Madrid (ES); Tania Matamoros Grande, Madrid (ES); David Abia Holgado, Madrid (ES); Verónica Barrioluengo Fernández, Madrid (ES)

(73) Assignee: CONSEJO SUPERIOR DE INVESTIGACIONES CIENTÍFICAS (CSIC), Madrid (ES)

( * ) Notice: Subject to any disclaimer, the term of this patent is extended or adjusted under 35 U.S.C. 154(b) by 0 days.

(21) Appl. No.: 14/891,950

(22) PCT Filed: May 8, 2014

(86) PCT No.: PCT/ES2014/070389
§ 371 (c)(1),
(2) Date: Nov. 17, 2015

(87) PCT Pub. No.: WO2014/184409
PCT Pub. Date: Nov. 20, 2014

(65) Prior Publication Data
US 2016/0090580 A1 Mar. 31, 2016

(30) Foreign Application Priority Data

May 17, 2013 (ES) .................................. 201330705

(51) Int. Cl.
C12N 9/12 (2006.01)
C12Q 1/64 (2006.01)
C12Q 1/68 (2006.01)
C12P 19/34 (2006.01)

(52) U.S. Cl.
CPC ............. *C12N 9/1276* (2013.01); *C12P 19/34* (2013.01); *C12Q 1/6869* (2013.01); *C12Y 207/07049* (2013.01)

(58) Field of Classification Search
CPC .......................... C12N 9/1241; C12Q 2531/00
See application file for complete search history.

(56) References Cited

FOREIGN PATENT DOCUMENTS

WO WO-2010130864 11/2010

OTHER PUBLICATIONS

English translation of PCT Written Opinion dated Jul. 16, 2014, PCT/ES2014/070389, 10 pages.

Alvarez, M., et al., "Altered error specificity of RNase H-deficient HIV-1 reverse transcriptases during DNA-dependent DNA synthesis", *Nucleic Acids Research*, vol. 41, No. 8, (2013), 4601-4612.

Alvarez, M., et al., "Increased Thermostability and Fidelity of DNA Synthesis of Wild-Type and Mutant HIV-1 Group O Reverse Transcriptases", *J. Mol. Biol.*, vol. 392, No. 4, (2009), 872-884.

Arezi, Bahram, et al., "Novel mutations in Moloney Murine Leukemia Virus reverse transcriptase increase thermostability through tighter binding to template-primer", *Nucleic Acids Research*, vol. 37, No. 2, (2009), 473-481.

Barrioluengo, Veronica, et al., "Thermostable HIV-1 group O reverse transcriptase variants with the same fidelity as murine leukaemia virus reverse transcriptase", *Biochemical Journal*, vol. 436, (2011), 599-607.

Bebenek, K., et al., "Analyzing Fidelity of DNA Polymerases", *Methods in Enzymology*, vol. 262, (1995), 217-232.

Boretto, Joelle, et al., "An Integrated System to Study Multiply Substituted Human Immunodeficiency Virus Type 1 Reverse Transcriptase", *Analytical Biochemistry*, vol. 292, (2001), 139-147.

Cote, Marie L., et al., "Murine leukemia virus reverse transcriptase: Structural comparison with HIV-1 reverse transcriptase", *Virus Research*, vol. 134, (2008), 186-202.

Curr, Kenneth, et al., "Influence of naturally occurring insertions in the fingers subdomain of human immunodeficiency virus type 1 reverse transcriptase on polymerase fidelity and mutation frequencies in vitro", *Journal of General Virology*, vol. 87, No. 2, (2003), 419-428.

De Leys, Robert, et al., "Isolation and Partial Characterization of an Unusual Human Immunodeficiency Retrovirus from Two Persons of West-Central African Origin", *Journal of Virology*, vol. 64, No. 3, (Mar. 1990), 1207-1216.

Gerard, Gary F., et al., "The role of template-primer in protection of reverse transciptase from thermal inactivation", *Nucleaic Acids Research*, vol. 30, No. 14, (2002), 3118-3129.

Hizi, Amnon, et al., "Retroviral reverse transcriptases (other than those of HIV-1 and murine leukemia virus): A comparison of their molecular and biochemical properties", *Virus Research*, vol. 134, (2008), 203-220.

(Continued)

*Primary Examiner* — Maryam Monshipouri
(74) *Attorney, Agent, or Firm* — Blakely Sokoloff Taylor & Zafman LLP

(57) ABSTRACT

The present invention falls within the field of biotechnology. More specifically, the invention relates to reverse transcriptases expressed and purified in bacteria and having the amino acid sequence of the reverse transcriptase of a human immunodeficiency virus type 1 (HIV-1) group O, modified at positions 358, 359 and 360; and variants of this enzyme that contain additional changes at positions 355 and 357 or at 478 or position 69 (in this case accompanied by an insertion of two amino acids). These polymerases have greater activity than the non-mutated enzyme at high temperatures (above 60° C.). In addition, they retain the capacity for DNA synthesis at temperatures greater than 70° C. Moreover, the copying fidelity of these enzymes is not significantly different from that of the non-mutated reverse transcriptase.

19 Claims, 6 Drawing Sheets

(56) References Cited

OTHER PUBLICATIONS

Le Grice, Stuart F., "Human Immunodeficiency Virus Reverse Transciptase: 25 Years of Research, Drug Discovery, and Promise", *The Journal of Biological Chemistry*, vol. 287, No. 49, (Nov. 30, 2012), 40850-40857.

Matamoros, Tania, et al., "Major Groove Binding Track Residues of the Connection Subdomain of Human Immunodeficiency Virus Type 1 Reverse Transcriptase Enhance cDNA Synthesis at High Temperatures", *Biochemistry*, vol. 52, (2013), 9318-9328.

Matamoros, Tania, et al., "Mechanistic Insights into the Role of Va175 of HIV-1 Reverse Transcriptase in Misinsertion and Mispair Extension Fidelity of DNA Synthesis", *J. Mol. Biol.*, vol. 375, (2008), 1234-1248.

Matamoros, Tania, et al., "Suppression of Multidrug-resistant HIV-1 Reverse Transcriptase Primer Unblocking Activity by alpha-Phosphate-modified Thymidine Analogues", *J. Mol. Biol.*, vol. 349, (2005), 451-463.

Menendez-Arias, Luis, et al., "Functional Characterization of Chimeric Reverse Transcriptases with Polypeptide Subunits of Highly Divergent HIV-1 Group M and O Strains", *Journal of Biological Chemistry*, vol. 276, No. 29, 2001, 27470-27479.

Quinones-Mateu, Miguel E., et al., "Characterization of the Reverse Transciptase of a Human Immunodeficiency Virus Type 1 Group O Isolate", *Virology*, vol. 236, No. 2, (1997), 364-373.

SEQUENCE LISTING

```
<160> NUMBER OF SEQ ID NOS: 20

<210> SEQ ID NO 1
<211> LENGTH: 560
<212> TYPE: PRT
<213> ORGANISM: HIV-1 group O

<400> SEQUENCE: 1

Pro Ile Ser Pro Ile Ala Pro Val Pro Lys Leu Lys Pro Gly Met
1               5                   10                  15

Asp Gly Pro Lys Val Lys Gln Trp Pro Leu Ser Lys Glu Lys Ile Glu
                20                  25                  30

Ala Leu Thr Ala Ile Cys Gln Glu Met Glu Gln Glu Gly Lys Ile Ser
            35                  40                  45

Arg Ile Gly Pro Glu Asn Pro Tyr Asn Thr Pro Ile Phe Ala Ile Lys
        50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Gly Gly Leu Lys Gln Lys Arg Ser Val Thr Val Leu Asp Val Gly
                100                 105                 110

Asp Ala Tyr Phe Ser Cys Pro Leu Asp Pro Asp Phe Arg Lys Tyr Thr
            115                 120                 125

Ala Phe Thr Ile Pro Ser Val Asn Asn Glu Thr Pro Gly Ile Arg Tyr
        130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Asp Pro Phe Arg Lys Asp Asn Pro
                165                 170                 175

Glu Leu Glu Ile Cys Gln Tyr Met Asp Asp Leu Tyr Val Gly Ser Asp
                180                 185                 190

Leu Pro Leu Ala Glu His Arg Lys Arg Val Glu Leu Leu Arg Glu His
            195                 200                 205

Leu Tyr Gln Trp Gly Phe Thr Thr Pro Asp Lys Lys His Gln Lys Glu
        210                 215                 220

Pro Pro Phe Met Trp Met Gly Tyr Glu Leu His Pro Asp Lys Trp Thr
225                 230                 235                 240

Val Gln Pro Ile Lys Leu Pro Asn Lys Asp Val Trp Thr Val Asn Asp
```

```
                245                 250                 255
Ile Gln Lys Leu Ile Gly Lys Leu Asn Trp Ala Ser Gln Ile Tyr Gln
            260                 265                 270

Gly Ile Arg Val Arg Glu Leu Cys Lys Leu Ile Arg Gly Thr Lys Ser
            275                 280                 285

Leu Thr Glu Val Val Pro Leu Ser Lys Glu Ala Glu Met Glu Leu Glu
            290                 295                 300

Glu Asn Arg Glu Lys Leu Lys Glu Pro Met His Gly Val Tyr Tyr Gln
305                 310                 315                 320

Pro Asp Lys Asp Leu Trp Val Asn Ile Gln Lys Gln Gly Glu Gly Gln
                325                 330                 335

Trp Thr Tyr Gln Ile Tyr Gln Asp Glu His Lys Asn Leu Lys Thr Gly
            340                 345                 350

Lys Tyr Thr Arg Gln Lys Ala Ser His Thr Asn Asp Ile Arg Gln Leu
            355                 360                 365

Ala Glu Val Ile Gln Lys Val Ser Gln Glu Ser Ile Val Ile Trp Gly
        370                 375                 380

Lys Leu Pro Lys Phe Lys Leu Pro Val Thr Arg Glu Thr Trp Glu Thr
385                 390                 395                 400

Trp Trp Ala Asp Tyr Trp Gln Ala Thr Trp Ile Pro Glu Trp Asp Tyr
                405                 410                 415

Val Ser Thr Pro Pro Leu Ile Lys Leu Trp Tyr Arg Leu Glu Ser Glu
            420                 425                 430

Pro Ile Arg Gly Ala Glu Thr Tyr Tyr Val Asp Gly Ala Ala Asn Arg
            435                 440                 445

Asp Thr Lys Leu Gly Lys Ala Gly Tyr Val Thr Glu Gln Gly Lys Gln
        450                 455                 460

Lys Ile Ile Lys Leu Asp Glu Thr Thr Asn Gln Lys Ala Glu Leu Met
465                 470                 475                 480

Ala Val Leu Leu Ala Leu Gln Asp Ser Lys Glu Lys Val Asn Ile Val
                485                 490                 495

Thr Asp Ser Gln Tyr Val Leu Gly Ile Ile Ser Ser Gln Pro Thr Gln
            500                 505                 510

Ser Glu Ser Pro Ile Val Gln Gln Ile Ile Glu Glu Leu Thr Lys Lys
            515                 520                 525

Glu Gln Val Tyr Leu Thr Trp Val Pro Ala His Lys Gly Ile Gly Gly
        530                 535                 540

Asn Glu Lys Ile Asp Lys Leu Val Ser Lys Asp Ile Arg Arg Val Leu
545                 550                 555                 560

<210> SEQ ID NO 2
<211> LENGTH: 1680
<212> TYPE: DNA
<213> ORGANISM: HIV-1 group O
<220> FEATURE:
<221> NAME/KEY: source
<222> LOCATION: 1..1680
<223> OTHER INFORMATION: /mol_type="unassigned DNA"
      /organism="HIV-1 group O"

<400> SEQUENCE: 2
cctataagcc ccatagcccc agtgccagta aagctaaaac caggaatgga tggaccaaaa      60
gtaaaacaat ggcccctatc taaagaaaaa atagaagcct taacagcaat atgccaggaa     120
atggaacaag aaggaaaaat ttcaagaata ggacctgaaa atccttataa tacacctatc     180
tttgctataa aaaagaaaga tagtactaag tggagaaagc tggtagactt tagggaatta     240
```

```
aacaagagaa cacaagattt tgggaggta cagttaggta tcccacatcc gggggtta      300
aagcaaaagc gatctgttac agtcttagat gtaggagatg cctatttctc atgccctta      360
gacccagatt ttagaaaata tactgctttc actattccta gtgtaaacaa tgagacccca      420
ggaataagat accagtacaa tgtcctcccg caaggatgga aaggttcgcc agccatattc      480
caaagttcaa tgacaaaaat tttagatcca tttaggaaag acaacccaga attagaaatt      540
tgtcagtaca tggatgacct atatgtagga tcagatttac ccctggcaga acatagaaaa      600
agggttgaat tgcttagaga acacttatat cagtggggat tcactacccc tgataaaaag      660
catcaaaagg aacctccctt tatgtggatg gggtatgagc tccatccaga taatggaca      720
gtacagccca tcaaattgcc taacaaagat gtgtggacag taatgatat acaaaaacta      780
ataggaaagt taaattgggc aagtcaaatc tatcaaggaa ttagagtaag agaattgtgt      840
aagttaatta gaggcaccaa gtcattaaca gaagtagtac cattaagcaa agaggcagag      900
atggaattag aggagaacag agagaaatta aagaaccaa tgcatggtgt atactatcaa      960
cctgataaag acttatgggt taatattcag aagcaaggag aagggcaatg gacttaccag     1020
atatatcagg atgaacataa gaaccctcaaa acagggaaat atactaggca aaaggcctcc     1080
cacacaaatg acataagaca attagcagaa gtaatccaga aggtgtctca agaatctata     1140
gttatctggg gaaattgcc taaatttaag ctgccagtca ctagagaaac ttgggaaaca     1200
tggtgggcag attattggca agccacctgg atcccagaat gggattatgt cagcacaccc     1260
ccattgatca aattatggta ccggttagaa agtgaaccta ttaggggggc agaaaccta     1320
tatgtagatg gagcagctaa tagagataca aaattaggaa aagcaggata tgttacagaa     1380
caagggaaac agaaaataat aaaattagat gagaccacca atcaaaaggc tgaattaatg     1440
gcagtattat tagccttaca ggattccaaa gaaaagtaa atatagtaac agactcacaa     1500
tatgtattgg gcattatctc ctcccagcct acacagagtg aatcccctat agttcagcag     1560
ataatagagg aactaacaaa aaaggaacag gtgtatctta catgggttcc tgctcataaa     1620
ggcataggag gaaatgaaaa aatagataaa ttagtaagca aggatattag aagagtcctc     1680
```

<210> SEQ ID NO 3
<211> LENGTH: 560
<212> TYPE: PRT
<213> ORGANISM: HIV-1 group O

<400> SEQUENCE: 3

```
Pro Ile Ser Pro Ile Ala Pro Val Pro Val Lys Leu Lys Pro Gly Met
1               5                   10                  15

Asp Gly Pro Lys Val Lys Gln Trp Pro Leu Ser Lys Glu Lys Ile Glu
            20                  25                  30

Ala Leu Thr Ala Ile Cys Gln Glu Met Glu Gln Glu Gly Lys Ile Ser
        35                  40                  45

Arg Ile Gly Pro Glu Asn Pro Tyr Asn Thr Pro Ile Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Gly Gly Leu Lys Gln Lys Arg Ser Val Thr Val Leu Asp Val Gly
            100                 105                 110

Asp Ala Tyr Phe Ser Cys Pro Leu Asp Pro Asp Phe Arg Lys Tyr Thr
```

-continued

```
            115                 120                 125
Ala Phe Thr Ile Pro Ser Val Asn Asn Glu Thr Pro Gly Ile Arg Tyr
130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Asp Pro Phe Arg Lys Asp Asn Pro
                165                 170                 175

Glu Leu Glu Ile Cys Gln Tyr Met Asp Asp Leu Tyr Val Gly Ser Asp
                180                 185                 190

Leu Pro Leu Ala Glu His Arg Lys Arg Val Glu Leu Leu Arg Glu His
                195                 200                 205

Leu Tyr Gln Trp Gly Phe Thr Thr Pro Asp Lys Lys His Gln Lys Glu
210                 215                 220

Pro Pro Phe Met Trp Met Gly Tyr Glu Leu His Pro Asp Lys Trp Thr
225                 230                 235                 240

Val Gln Pro Ile Lys Leu Pro Asn Lys Asp Val Trp Thr Val Asn Asp
                245                 250                 255

Ile Gln Lys Leu Ile Gly Lys Leu Asn Trp Ala Ser Gln Ile Tyr Gln
                260                 265                 270

Gly Ile Arg Val Arg Glu Leu Cys Lys Leu Ile Arg Gly Thr Lys Ser
                275                 280                 285

Leu Thr Glu Val Val Pro Leu Ser Lys Glu Ala Glu Met Glu Leu Glu
290                 295                 300

Glu Asn Arg Glu Lys Leu Lys Glu Pro Met His Gly Val Tyr Tyr Gln
305                 310                 315                 320

Pro Asp Lys Asp Leu Trp Val Asn Ile Gln Lys Gln Gly Glu Gly Gln
                325                 330                 335

Trp Thr Tyr Gln Ile Tyr Gln Asp Glu His Lys Asn Leu Lys Thr Gly
                340                 345                 350

Lys Tyr Thr Arg Gln Arg Gly Ala His Thr Asn Asp Ile Arg Gln Leu
                355                 360                 365

Ala Glu Val Ile Gln Lys Val Ser Gln Glu Ser Ile Val Ile Trp Gly
370                 375                 380

Lys Leu Pro Lys Phe Lys Leu Pro Val Thr Arg Glu Thr Trp Glu Thr
385                 390                 395                 400

Trp Trp Ala Asp Tyr Trp Gln Ala Thr Trp Ile Pro Glu Trp Asp Tyr
                405                 410                 415

Val Ser Thr Pro Pro Leu Ile Lys Leu Trp Tyr Arg Leu Glu Ser Glu
                420                 425                 430

Pro Ile Arg Gly Ala Glu Thr Tyr Tyr Val Asp Gly Ala Ala Asn Arg
                435                 440                 445

Asp Thr Lys Leu Gly Lys Ala Gly Tyr Val Thr Glu Gln Gly Lys Gln
                450                 455                 460

Lys Ile Ile Lys Leu Asp Glu Thr Thr Asn Gln Lys Ala Glu Leu Met
465                 470                 475                 480

Ala Val Leu Leu Ala Leu Gln Asp Ser Lys Glu Lys Val Asn Ile Val
                485                 490                 495

Thr Asp Ser Gln Tyr Val Leu Gly Ile Ile Ser Ser Gln Pro Thr Gln
                500                 505                 510

Ser Glu Ser Pro Ile Val Gln Gln Ile Glu Glu Leu Thr Lys Lys
                515                 520                 525

Glu Gln Val Tyr Leu Thr Trp Val Pro Ala His Lys Gly Ile Gly Gly
530                 535                 540
```

Asn Glu Lys Ile Asp Lys Leu Val Ser Lys Asp Ile Arg Arg Val Leu
545                 550                 555                 560

<210> SEQ ID NO 4
<211> LENGTH: 1680
<212> TYPE: DNA
<213> ORGANISM: HIV-1 group O
<220> FEATURE:
<221> NAME/KEY: source
<222> LOCATION: 1..1680
<223> OTHER INFORMATION: /mol_type="unassigned DNA"
      /organism="HIV-1 group O"

<400> SEQUENCE: 4

```
cctataagcc ccatagcccc agtgccagta aagctaaaac caggaatgga tggaccaaaa      60
gtaaaacaat ggcccctatc taagaaaaaa atagaagcct taacagcaat atgccaggaa     120
atggaacaag aaggaaaaat ttcaagaata ggacctgaaa atccttataa tacacctatc     180
tttgctataa aaaagaaaga tagtactaag tggagaaagc tggtagactt tagggaatta     240
aacaagagaa cacaagattt tgggaggta cagttaggta tcccacatcc gggggttta      300
aagcaaaagc gatctgttac agtcttagat gtaggagatg cctatttctc atgccccttta     360
gacccagatt ttagaaaata tactgctttc actattccta gtgtaaacaa tgagacccca     420
ggataagat accagtacaa tgtcctcccg caaggatgga aggttcgcc agccatattc      480
caaagttcaa tgacaaaaat tttagatcca tttaggaaag caacccaga attagaaatt      540
tgtcagtaca tggatgacct atatgtagga tcagatttac ccctggcaga acatagaaaa     600
agggttgaat tgcttagaga acacttatat cagtggggat tcactacccc tgataaaaag     660
catcaaaagg aacctccctt tatgtggatg gggtatgagc tccatccaga taatggaca      720
gtacagccca tcaaattgcc taacaaagat gtgtggacag taaatgatat acaaaaacta     780
ataggaaagt taaattgggc aagtcaaatc tatcaaggaa ttagagtaag gaattgtgt     840
aagttaatta gaggcaccaa gtcattaaca gaagtagtac cattaagcaa agaggcagag     900
atggaattag aggagaacag agagaaatta aagaaccaa tgcatggtgt atactatcaa     960
cctgataaag acttatgggt taatattcag aagcaaggag aagggcaatg gacttaccag    1020
atatatcagg atgaacataa gaacctcaaa acagggaaat atactaggca aaggggcgcc    1080
cacacaaatg acataagaca attagcagaa gtaatccaga aggtgtctca agaatctata    1140
gttatctggg gaaaattgcc taaatttaag ctgccagtca ctagagaaac ttgggaaaca    1200
tggtgggcag attattggca agccacctgg atcccagaat gggattatgt cagcacaccc    1260
ccattgatca aattatggta ccggttagaa agtgaaccta ttaggggggc agaaacctat    1320
tatgtagatg gagcagctaa tagagataca aaattaggaa aagcaggata tgttacagaa    1380
caagggaaac agaaaataat aaaattagat gagaccacca atcaaaaggc tgaattaatg    1440
gcagtattat tagccttaca ggattccaaa gaaaagtaa atatagtaac agactcacaa    1500
tatgtattgg gcattatctc ctcccagcct acacagagtg aatcccctat agttcagcag    1560
ataatagagg aactaacaaa aaaggaacag gtgtatctta catgggttcc tgctcataaa    1620
ggcataggag gaaatgaaaa aatagataaa ttagtaagca aggatattag aagagtcctc    1680
```

<210> SEQ ID NO 5
<211> LENGTH: 560
<212> TYPE: PRT
<213> ORGANISM: HIV-1 group O

<400> SEQUENCE: 5

```
Pro Ile Ser Pro Ile Ala Pro Val Pro Val Lys Leu Lys Pro Gly Met
1               5                   10                  15

Asp Gly Pro Lys Val Lys Gln Trp Pro Leu Ser Lys Glu Lys Ile Glu
            20                  25                  30

Ala Leu Thr Ala Ile Cys Gln Glu Met Glu Gln Glu Gly Lys Ile Ser
        35                  40                  45

Arg Ile Gly Pro Glu Asn Pro Tyr Asn Thr Pro Ile Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Gly Gly Leu Lys Gln Lys Arg Ser Val Thr Val Leu Asp Val Gly
            100                 105                 110

Asp Ala Tyr Phe Ser Cys Pro Leu Asp Pro Asp Phe Arg Lys Tyr Thr
        115                 120                 125

Ala Phe Thr Ile Pro Ser Val Asn Asn Glu Thr Pro Gly Ile Arg Tyr
    130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Asp Pro Phe Arg Lys Asp Asn Pro
                165                 170                 175

Glu Leu Glu Ile Cys Gln Tyr Met Asp Asp Leu Tyr Val Gly Ser Asp
            180                 185                 190

Leu Pro Leu Ala Glu His Arg Lys Arg Val Glu Leu Leu Arg Glu His
        195                 200                 205

Leu Tyr Gln Trp Gly Phe Thr Thr Pro Asp Lys Lys His Gln Lys Glu
    210                 215                 220

Pro Pro Phe Met Trp Met Gly Tyr Glu Leu His Pro Asp Lys Trp Thr
225                 230                 235                 240

Val Gln Pro Ile Lys Leu Pro Asn Lys Asp Val Trp Thr Val Asn Asp
                245                 250                 255

Ile Gln Lys Leu Ile Gly Lys Leu Asn Trp Ala Ser Gln Ile Tyr Gln
            260                 265                 270

Gly Ile Arg Val Arg Glu Leu Cys Lys Leu Ile Arg Gly Thr Lys Ser
        275                 280                 285

Leu Thr Glu Val Val Pro Leu Ser Lys Glu Ala Glu Met Glu Leu Glu
    290                 295                 300

Glu Asn Arg Glu Lys Leu Lys Glu Pro Met His Gly Val Tyr Tyr Gln
305                 310                 315                 320

Pro Asp Lys Asp Leu Trp Val Asn Ile Gln Lys Gln Gly Glu Gly Gln
                325                 330                 335

Trp Thr Tyr Gln Ile Tyr Gln Asp Glu His Lys Asn Leu Lys Thr Gly
            340                 345                 350

Lys Tyr Ala Arg Met Arg Gly Ala His Thr Asn Asp Ile Arg Gln Leu
        355                 360                 365

Ala Glu Val Ile Gln Lys Val Ser Gln Glu Ser Ile Val Ile Trp Gly
    370                 375                 380

Lys Leu Pro Lys Phe Lys Leu Pro Val Thr Arg Glu Thr Trp Glu Thr
385                 390                 395                 400

Trp Trp Ala Asp Tyr Trp Gln Ala Thr Trp Ile Pro Glu Trp Asp Tyr
                405                 410                 415
```

```
Val Ser Thr Pro Pro Leu Ile Lys Leu Trp Tyr Arg Leu Glu Ser Glu
            420                 425                 430

Pro Ile Arg Gly Ala Glu Thr Tyr Tyr Val Asp Gly Ala Ala Asn Arg
            435                 440                 445

Asp Thr Lys Leu Gly Lys Ala Gly Tyr Val Thr Glu Gln Gly Lys Gln
            450                 455                 460

Lys Ile Ile Lys Leu Asp Glu Thr Thr Asn Gln Lys Ala Glu Leu Met
465                 470                 475                 480

Ala Val Leu Leu Ala Leu Gln Asp Ser Lys Glu Lys Val Asn Ile Val
            485                 490                 495

Thr Asp Ser Gln Tyr Val Leu Gly Ile Ile Ser Ser Gln Pro Thr Gln
            500                 505                 510

Ser Glu Ser Pro Ile Val Gln Gln Ile Ile Glu Glu Leu Thr Lys Lys
            515                 520                 525

Glu Gln Val Tyr Leu Thr Trp Val Pro Ala His Lys Gly Ile Gly Gly
            530                 535                 540

Asn Glu Lys Ile Asp Lys Leu Val Ser Lys Asp Ile Arg Arg Val Leu
545                 550                 555                 560
```

<210> SEQ ID NO 6
<211> LENGTH: 1680
<212> TYPE: DNA
<213> ORGANISM: HIV-1 group O
<220> FEATURE:
<221> NAME/KEY: source
<222> LOCATION: 1..1680
<223> OTHER INFORMATION: /mol_type="unassigned DNA"
      /organism="HIV-1 group O"

<400> SEQUENCE: 6

```
cctataagcc ccatagcccc agtgccagta aagctaaaac caggaatgga tggaccaaaa      60
gtaaaacaat ggcccctatc taaagaaaaa atagaagcct taacagcaat atgccaggaa     120
atggaacaag aaggaaaaat tcaagaata ggaccctgaaa atccttataa tacacctatc     180
tttgctataa aaaagaaaga tagtactaag tggagaaagc tggtagactt tagggaatta     240
aacaagagaa cacaagattt tgggaggta cagttaggta tcccacatcc gggggggttta     300
aagcaaaagc gatctgttac agtcttagat gtaggagatg cctatttctc atgcccctta     360
gacccagatt ttagaaaata tactgctttc actattccta gtgtaaacaa tgagaccca      420
ggaataagat accagtacaa tgtcctcccg caaggatgga aggttcgcc agccatattc      480
caaagttcaa tgcacaaaat tttagatcca tttaggaaag acaacccaga attagaaatt      540
tgtcagtaca tggatgacct atatgtagga tcagatttac ccctggcaga acatagaaaa      600
agggttgaat tgcttagaga acacttatat cagtggggat tcactacccc tgataaaaag      660
catcaaaagg aacctccctt tatgtggatg gggtatgagc tccatccaga taatggaca      720
gtacagccca tcaaattgcc taacaaagat gtgtggacag taatgatat acaaaaacta      780
ataggaaagt taaattgggc aagtcaaatc tatcaaggaa ttagagtaag agaattgtgt      840
aagttaatta gaggcaccaa gtcattaaca gaagtagtac cattaagcaa agaggcagag      900
atggaattag aggagaacag agagaaatta aagaaccca tgcatggtgt atactatcaa      960
cctgataaag acttatgggt taatattcag aagcaaggag aagggcaatg gacttaccag     1020
atatatcagg atgaacataa gaaccctcaaa acagggaaat atgctaggat gaggggcgcc     1080
cacacaaatg acataagaca attagcagaa gtaatccaga aggtgtctca agaatctata     1140
```

```
gttatctggg gaaaattgcc taaatttaag ctgccagtca ctagagaaac ttgggaaaca    1200
tggtgggcag attattggca agccacctgg atcccagaat gggattatgt cagcacaccc    1260
ccattgatca aattatggta ccggttagaa agtgaaccta ttagggggc agaaacctat     1320 tatgtagatg gagcagctaa tagagataca aaattaggaa aagcaggata tgttacagaa    1380
caagggaaac agaaaataat aaaattagat gagaccacca atcaaaaggc tgaattaatg    1440
gcagtattat tagccttaca ggattccaaa gaaaaagtaa atatagtaac agactcacaa    1500
tatgtattgg gcattatctc ctcccagcct acacagagtg aatcccctat agttcagcag    1560
ataatagagg aactaacaaa aaaggaacag gtgtatctta catgggttcc tgctcataaa    1620
ggcataggag gaaatgaaaa aatagataaa ttagtaagca aggatattag aagagtcctc    1680
```

<210> SEQ ID NO 7
<211> LENGTH: 562
<212> TYPE: PRT
<213> ORGANISM: HIV-1 group O

<400> SEQUENCE: 7

```
Pro Ile Ser Pro Ile Ala Pro Val Pro Val Lys Leu Lys Pro Gly Met
1               5                   10                  15

Asp Gly Pro Lys Val Lys Gln Trp Pro Leu Ser Lys Glu Lys Ile Glu
            20                  25                  30

Ala Leu Thr Ala Ile Cys Gln Glu Met Glu Gln Glu Gly Lys Ile Ser
        35                  40                  45

Arg Ile Gly Pro Glu Asn Pro Tyr Asn Thr Pro Ile Phe Ala Ile Lys
    50                  55                  60

Lys Lys Asp Ser Ser Gly Lys Trp Arg Lys Leu Val Asp Phe Arg
65                  70                  75                  80

Glu Leu Asn Lys Arg Thr Gln Asp Phe Trp Glu Val Gln Leu Gly Ile
                85                  90                  95

Pro His Pro Gly Gly Leu Lys Gln Lys Arg Ser Val Thr Val Leu Asp
            100                 105                 110

Val Gly Asp Ala Tyr Phe Ser Cys Pro Leu Asp Pro Asp Phe Arg Lys
        115                 120                 125

Tyr Thr Ala Phe Thr Ile Pro Ser Val Asn Asn Glu Thr Pro Gly Ile
    130                 135                 140

Arg Tyr Gln Tyr Asn Val Leu Pro Gln Gly Trp Lys Gly Ser Pro Ala
145                 150                 155                 160

Ile Phe Gln Ser Ser Met Thr Lys Ile Leu Asp Pro Phe Arg Lys Asp
                165                 170                 175

Asn Pro Glu Leu Glu Ile Cys Gln Tyr Met Asp Asp Leu Tyr Val Gly
            180                 185                 190

Ser Asp Leu Pro Leu Ala Glu His Arg Lys Arg Val Glu Leu Leu Arg
        195                 200                 205

Glu His Leu Tyr Gln Trp Gly Phe Thr Thr Pro Asp Lys Lys His Gln
    210                 215                 220

Lys Glu Pro Pro Phe Met Trp Met Gly Tyr Glu Leu His Pro Asp Lys
225                 230                 235                 240

Trp Thr Val Gln Pro Ile Lys Leu Pro Asn Lys Asp Val Trp Thr Val
                245                 250                 255

Asn Asp Ile Gln Lys Leu Ile Gly Lys Leu Asn Trp Ala Ser Gln Ile
            260                 265                 270

Tyr Gln Gly Ile Arg Val Arg Glu Leu Cys Lys Leu Ile Arg Gly Thr
        275                 280                 285
```

Lys Ser Leu Thr Glu Val Val Pro Leu Ser Lys Glu Ala Glu Met Glu
            290                 295                 300

Leu Glu Glu Asn Arg Glu Lys Leu Lys Glu Pro Met His Gly Val Tyr
305                 310                 315                 320

Tyr Gln Pro Asp Lys Asp Leu Trp Val Asn Ile Gln Lys Gln Gly Glu
                325                 330                 335

Gly Gln Trp Thr Tyr Gln Ile Tyr Gln Asp Glu His Lys Asn Leu Lys
            340                 345                 350

Thr Gly Lys Tyr Thr Arg Gln Arg Gly Ala His Thr Asn Asp Ile Arg
            355                 360                 365

Gln Leu Ala Glu Val Ile Gln Lys Val Ser Gln Glu Ser Ile Val Ile
            370                 375                 380

Trp Gly Lys Leu Pro Lys Phe Lys Leu Pro Val Thr Arg Glu Thr Trp
385                 390                 395                 400

Glu Thr Trp Trp Ala Asp Tyr Trp Gln Ala Thr Trp Ile Pro Glu Trp
                405                 410                 415

Asp Tyr Val Ser Thr Pro Pro Leu Ile Lys Leu Trp Tyr Arg Leu Glu
                420                 425                 430

Ser Glu Pro Ile Arg Gly Ala Glu Thr Tyr Tyr Val Asp Gly Ala Ala
            435                 440                 445

Asn Arg Asp Thr Lys Leu Gly Lys Ala Gly Tyr Val Thr Glu Gln Gly
450                 455                 460

Lys Gln Lys Ile Ile Lys Leu Asp Glu Thr Thr Asn Gln Lys Ala Glu
465                 470                 475                 480

Leu Met Ala Val Leu Leu Ala Leu Gln Asp Ser Lys Glu Lys Val Asn
                485                 490                 495

Ile Val Thr Asp Ser Gln Tyr Val Leu Gly Ile Ile Ser Ser Gln Pro
                500                 505                 510

Thr Gln Ser Glu Ser Pro Ile Val Gln Gln Ile Ile Glu Glu Leu Thr
            515                 520                 525

Lys Lys Glu Gln Val Tyr Leu Thr Trp Val Pro Ala His Lys Gly Ile
530                 535                 540

Gly Gly Asn Glu Lys Ile Asp Lys Leu Val Ser Lys Asp Ile Arg Arg
545                 550                 555                 560

Val Leu

<210> SEQ ID NO 8
<211> LENGTH: 1686
<212> TYPE: DNA
<213> ORGANISM: HIV-1 group O
<220> FEATURE:
<221> NAME/KEY: source
<222> LOCATION: 1..1686
<223> OTHER INFORMATION: /mol_type="unassigned DNA"
      /organism="HIV-1 group O"

<400> SEQUENCE: 8
cctataagcc ccatagcccc agtgccagta aagctaaaac caggaatgga tggaccaaaa      60
gtaaaacaat ggcccctatc taaagaaaaa atagaagcct taacagcaat atgccaggaa     120
atggaacaag aaggaaaaat ttcaagaata ggacctgaaa atccttataa tacacctatc     180
tttgctataa aaagaaaaga tagtagttcc gggaagtgga gaagctggt agactttagg      240 gaattaaaca agagaacaca agattttttgg gaggtacagt taggtatccc acatccgggg     300
ggtttaaagc aaaagcgatc tgttacagtc ttagatgtag gagatgccta tttctcatgc     360

```
ccctttagacc cagattttag aaaatatact gctttcacta ttcctagtgt aaacaatgag   420
accccaggaa taagatacca gtacaatgtc ctcccgcaag gatggaaagg ttcgccagcc   480
atattccaaa gttcaatgac aaaaatttta gatccattta ggaaagacaa cccagaatta   540
gaaatttgtc agtacatgga tgacctatat gtaggatcag atttaccccct ggcagaacat   600
agaaaaaggg ttgaattgct tagagaacac ttatatcagt ggggattcac taccccctgat   660
aaaaagcatc aaaggaacc tcccttatg tggatgggt atgagctcca tccagataaa   720
tggacagtac agcccatcaa attgcctaac aaagatgtgt ggacagtaaa tgatatacaa   780
aaactaatag gaaagttaaa ttgggcaagt caaatctatc aaggaattag agtaagagaa   840
ttgtgtaagt taattagagg caccaagtca ttaacagaag tagtaccatt aagcaaagag   900
gcagagatgg aattagagga gaacagagag aaattaaaag aaccaatgca tggtgtatac   960
tatcaacctg ataaagactt atgggttaat attcagaagc aaggagaagg gcaatggact  1020
taccagatat atcaggatga acataagaac ctcaaaacag ggaaatatac taggcaaagg  1080
ggcgcccaca caaatgacat aagacaatta gcagaagtaa tccagaaggt gtctcaagaa  1140
tctatagtta tctggggaaa attgcctaaa tttaagctgc cagtcactag agaaacttgg  1200
gaaacatggt gggcagatta ttggcaagcc acctggatcc cagaatggga ttatgtcagc  1260
acaccccccat tgatcaaatt atggtaccgg ttagaaagtg aacctattag ggggcagaa  1320
acctattatg tagatggagc agctaataga gatacaaaat taggaaaagc aggatatgtt  1380
acagaacaag ggaaacagaa aataataaaa ttagatgaga ccaccaatca aaaggctgaa  1440
ttaatggcag tattattagc cttacaggat tccaaagaaa agtaaatat agtaacagac  1500
tcacaatatg tattgggcat tatctcctcc cagcctacac agagtgaatc ccctatagtt  1560
cagcagataa tagaggaact aacaaaaaag gaacaggtgt atcttacatg ggttcctgct  1620
cataaaggca taggaggaaa tgaaaaaata gataaattag taagcaagga tattagaaga  1680
gtcctc                                                              1686
```

<210> SEQ ID NO 9
<211> LENGTH: 560
<212> TYPE: PRT
<213> ORGANISM: HIV-1 group O

<400> SEQUENCE: 9

```
Pro Ile Ser Pro Ile Ala Pro Val Pro Val Lys Leu Lys Pro Gly Met
1               5                   10                  15

Asp Gly Pro Lys Val Lys Gln Trp Pro Leu Ser Lys Glu Lys Ile Glu
            20                  25                  30

Ala Leu Thr Ala Ile Cys Gln Glu Met Glu Gln Glu Gly Lys Ile Ser
        35                  40                  45

Arg Ile Gly Pro Glu Asn Pro Tyr Asn Thr Pro Ile Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Gly Gly Leu Lys Gln Lys Arg Ser Val Thr Val Leu Asp Val Gly
            100                 105                 110

Asp Ala Tyr Phe Ser Cys Pro Leu Asp Pro Asp Phe Arg Lys Tyr Thr
        115                 120                 125

Ala Phe Thr Ile Pro Ser Val Asn Asn Glu Thr Pro Gly Ile Arg Tyr
```

-continued

```
            130                 135                 140
Gln Tyr Asn Val Leu Pro Gln Gly Trp Lys Gly Ser Pro Ala Ile Phe
145                 150                 155                 160

Gln Ser Ser Met Thr Lys Ile Leu Asp Pro Phe Arg Lys Asp Asn Pro
                    165                 170                 175

Glu Leu Glu Ile Cys Gln Tyr Met Asp Asp Leu Tyr Val Gly Ser Asp
                180                 185                 190

Leu Pro Leu Ala Glu His Arg Lys Arg Val Glu Leu Leu Arg Glu His
            195                 200                 205

Leu Tyr Gln Trp Gly Phe Thr Thr Pro Asp Lys Lys His Gln Lys Glu
210                 215                 220

Pro Pro Phe Met Trp Met Gly Tyr Glu Leu His Pro Asp Lys Trp Thr
225                 230                 235                 240

Val Gln Pro Ile Lys Leu Pro Asn Lys Asp Val Trp Thr Val Asn Asp
                    245                 250                 255

Ile Gln Lys Leu Ile Gly Lys Leu Asn Trp Ala Ser Gln Ile Tyr Gln
                260                 265                 270

Gly Ile Arg Val Arg Glu Leu Cys Lys Leu Ile Arg Gly Thr Lys Ser
            275                 280                 285

Leu Thr Glu Val Val Pro Leu Ser Lys Glu Ala Glu Met Glu Leu Glu
        290                 295                 300

Glu Asn Arg Glu Lys Leu Lys Glu Pro Met His Gly Val Tyr Tyr Gln
305                 310                 315                 320

Pro Asp Lys Asp Leu Trp Val Asn Ile Gln Lys Gln Gly Glu Gly Gln
                    325                 330                 335

Trp Thr Tyr Gln Ile Tyr Gln Asp Glu His Lys Asn Leu Lys Thr Gly
                340                 345                 350

Lys Tyr Thr Arg Gln Arg Gly Ala His Thr Asn Asp Ile Arg Gln Leu
            355                 360                 365

Ala Glu Val Ile Gln Lys Val Ser Gln Glu Ser Ile Val Ile Trp Gly
        370                 375                 380

Lys Leu Pro Lys Phe Lys Leu Pro Val Thr Arg Glu Thr Trp Glu Thr
385                 390                 395                 400

Trp Trp Ala Asp Tyr Trp Gln Ala Thr Trp Ile Pro Glu Trp Asp Tyr
                    405                 410                 415

Val Ser Thr Pro Pro Leu Ile Lys Leu Trp Tyr Arg Leu Glu Ser Glu
                420                 425                 430

Pro Ile Arg Gly Ala Glu Thr Tyr Tyr Val Asp Gly Ala Ala Asn Arg
            435                 440                 445

Asp Thr Lys Leu Gly Lys Ala Gly Tyr Val Thr Glu Gln Gly Lys Gln
        450                 455                 460

Lys Ile Ile Lys Leu Asp Glu Thr Thr Asn Gln Lys Ala Gln Leu Met
465                 470                 475                 480

Ala Val Leu Leu Ala Leu Gln Asp Ser Lys Glu Lys Val Asn Ile Val
                    485                 490                 495

Thr Asp Ser Gln Tyr Val Leu Gly Ile Ile Ser Ser Gln Pro Thr Gln
                500                 505                 510

Ser Glu Ser Pro Ile Val Gln Gln Ile Glu Glu Leu Thr Lys Lys
            515                 520                 525

Glu Gln Val Tyr Leu Thr Trp Val Pro Ala His Lys Gly Ile Gly Gly
        530                 535                 540

Asn Glu Lys Ile Asp Lys Leu Val Ser Lys Asp Ile Arg Arg Val Leu
545                 550                 555                 560
```

<210> SEQ ID NO 10
<211> LENGTH: 1680
<212> TYPE: DNA
<213> ORGANISM: HIV-1 group O
<220> FEATURE:
<221> NAME/KEY: source
<222> LOCATION: 1..1680
<223> OTHER INFORMATION: /mol_type="unassigned DNA"
      /organism="HIV-1 group O"

<400> SEQUENCE: 10

| | | | | | |
|---|---|---|---|---|---|
| cctataagcc | ccatagcccc | agtgccagta | aagctaaaac | caggaatgga | tggaccaaaa | 60 |
| gtaaaacaat | ggcccctatc | taagaaaaaa | atagaagcct | aacagcaat | atgccaggaa | 120 |
| atggaacaag | aaggaaaaat | ttcaagaata | ggacctgaaa | atccttataa | tacacctatc | 180 |
| tttgctataa | aaagaaaga | tagtactaag | tggagaaagc | tggtagactt | tagggaatta | 240 |
| aacaagagaa | cacaagattt | tgggaggta | cagttaggta | tcccacatcc | gggggttta | 300 |
| aagcaaaagc | gatctgttac | agtcttagat | gtaggagatg | cctatttctc | atgccccta | 360 |
| gacccagatt | ttagaaaata | tactgctttc | actattccta | gtgtaaacaa | tgagaccca | 420 |
| ggaataagat | accagtacaa | tgtcctcccg | caaggatgga | aaggttcgcc | agccatattc | 480 |
| caaagttcaa | tgacaaaaat | tttagatcca | tttaggaaag | acaacccaga | attagaaatt | 540 |
| tgtcagtaca | tggatgacct | atatgtagga | tcagatttac | ccctggcaga | acatagaaaa | 600 |
| agggttgaat | tgcttagaga | acacttatat | cagtggggat | tcactacccc | tgataaaaag | 660 |
| catcaaaagg | aacctccctt | tatgtggatg | gggtatgagc | tccatccaga | taatgggaca | 720 |
| gtacagccca | tcaaattgcc | taacaaagat | gtgtggacag | taatgatat | acaaaaacta | 780 |
| ataggaaagt | taaattgggc | aagtcaaatc | tatcaaggaa | ttagagtaag | agaattgtgt | 840 |
| aagttaatta | gaggcaccaa | gtcattaaca | gaagtagtac | cattaagcaa | agaggcagag | 900 |
| atggaattag | aggagaacag | agagaaatta | aagaaccaa | tgcatggtgt | atactatcaa | 960 |
| cctgataaag | acttatgggt | taatattcag | aagcaaggag | aagggcaatg | gacttaccag | 1020 |
| atatatcagg | atgaacataa | gaacctcaaa | acagggaaat | atactaggca | aggggcgcc | 1080 |
| cacacaaatg | acataagaca | attagcagaa | gtaatccaga | aggtgtctca | agaatctata | 1140 |
| gttatctggg | gaaaattgcc | taaatttaag | ctgccagtca | ctagagaaac | ttggaaaca | 1200 |
| tggtgggcag | attattggca | agccacctgg | atcccagaat | gggattatgt | cagcacaccc | 1260 |
| ccattgatca | aattatggta | ccggttagaa | agtgaaccta | ttaggggggc | agaaacctat | 1320 |
| tatgtagatg | gagcagctaa | tagagataca | aaattaggaa | aagcaggata | tgttacagaa | 1380 |
| caagggaaac | agaaaataat | aaaattagat | gagaccacca | atcaaaaggc | tcaattaatg | 1440 |
| gcagtattat | tagccttaca | ggattccaaa | gaaaagtaa | atatagtaac | agactcacaa | 1500 |
| tatgtattgg | gcattatctc | ctcccagcct | acacagagtg | aatcccctat | agttcagcag | 1560 |
| ataatagagg | aactaacaaa | aaaggaacag | gtgtatctta | catgggttcc | tgctcataaa | 1620 |
| ggcataggag | gaaatgaaaa | aatagataaa | ttagtaagca | aggatattag | aagagtcctc | 1680 |

<210> SEQ ID NO 11
<211> LENGTH: 572
<212> TYPE: PRT
<213> ORGANISM: HIV-1 group O

<400> SEQUENCE: 11

Met Asn Ser Pro Ile Ser Pro Ile Ala Pro Val Pro Val Lys Leu Lys

```
1               5                   10                  15
Pro Gly Met Asp Gly Pro Lys Val Lys Gln Trp Pro Leu Ser Lys Glu
                20                  25                  30
Lys Ile Glu Ala Leu Thr Ala Ile Cys Gln Glu Met Glu Gln Glu Gly
                35                  40                  45
Lys Ile Ser Arg Ile Gly Pro Glu Asn Pro Tyr Asn Thr Pro Ile Phe
                50                  55                  60
Ala Ile Lys Lys Lys Asp Ser Thr Lys Trp Arg Lys Leu Val Asp Phe
65                  70                  75                  80
Arg Glu Leu Asn Lys Arg Thr Gln Asp Phe Trp Glu Val Gln Leu Gly
                85                  90                  95
Ile Pro His Pro Gly Gly Leu Lys Gln Lys Arg Ser Val Thr Val Leu
                100                 105                 110
Asp Val Gly Asp Ala Tyr Phe Ser Cys Pro Leu Asp Pro Asp Phe Arg
                115                 120                 125
Lys Tyr Thr Ala Phe Thr Ile Pro Ser Val Asn Asn Glu Thr Pro Gly
                130                 135                 140
Ile Arg Tyr Gln Tyr Asn Val Leu Pro Gln Gly Trp Lys Gly Ser Pro
145                 150                 155                 160
Ala Ile Phe Gln Ser Ser Met Thr Lys Ile Leu Asp Pro Phe Arg Lys
                165                 170                 175
Asp Asn Pro Glu Leu Glu Ile Cys Gln Tyr Met Asp Asp Leu Tyr Val
                180                 185                 190
Gly Ser Asp Leu Pro Leu Ala Glu His Arg Lys Arg Val Glu Leu Leu
                195                 200                 205
Arg Glu His Leu Tyr Gln Trp Gly Phe Thr Thr Pro Asp Lys Lys His
                210                 215                 220
Gln Lys Glu Pro Pro Phe Met Trp Met Gly Tyr Glu Leu His Pro Asp
225                 230                 235                 240
Lys Trp Thr Val Gln Pro Ile Lys Leu Pro Asn Lys Asp Val Trp Thr
                245                 250                 255
Val Asn Asp Ile Gln Lys Leu Ile Gly Lys Leu Asn Trp Ala Ser Gln
                260                 265                 270
Ile Tyr Gln Gly Ile Arg Val Arg Glu Leu Cys Lys Leu Ile Arg Gly
                275                 280                 285
Thr Lys Ser Leu Thr Glu Val Val Pro Leu Ser Lys Glu Ala Glu Met
                290                 295                 300
Glu Leu Glu Glu Asn Arg Glu Lys Leu Lys Glu Pro Met His Gly Val
305                 310                 315                 320
Tyr Tyr Gln Pro Asp Lys Asp Leu Trp Val Asn Ile Gln Lys Gln Gly
                325                 330                 335
Glu Gly Gln Trp Thr Tyr Gln Ile Tyr Gln Asp Glu His Lys Asn Leu
                340                 345                 350
Lys Thr Gly Lys Tyr Thr Arg Gln Lys Ala Ser His Thr Asn Asp Ile
                355                 360                 365
Arg Gln Leu Ala Glu Val Ile Gln Lys Val Ser Gln Glu Ser Ile Val
                370                 375                 380
Ile Trp Gly Lys Leu Pro Lys Phe Lys Leu Pro Val Thr Arg Glu Thr
385                 390                 395                 400
Trp Glu Thr Trp Trp Ala Asp Tyr Trp Gln Ala Thr Trp Ile Pro Glu
                405                 410                 415
Trp Asp Tyr Val Ser Thr Pro Pro Leu Ile Lys Leu Trp Tyr Arg Leu
                420                 425                 430
```

```
Glu Ser Glu Pro Ile Arg Gly Ala Glu Thr Tyr Tyr Val Asp Gly Ala
        435                 440                 445

Ala Asn Arg Asp Thr Lys Leu Gly Lys Ala Gly Tyr Val Thr Glu Gln
    450                 455                 460

Gly Lys Gln Lys Ile Ile Lys Leu Asp Glu Thr Thr Asn Gln Lys Ala
465                 470                 475                 480

Glu Leu Met Ala Val Leu Leu Ala Leu Gln Asp Ser Lys Glu Lys Val
                485                 490                 495

Asn Ile Val Thr Asp Ser Gln Tyr Val Leu Gly Ile Ile Ser Ser Gln
            500                 505                 510

Pro Thr Gln Ser Glu Ser Pro Ile Val Gln Gln Ile Ile Glu Glu Leu
        515                 520                 525

Thr Lys Lys Glu Gln Val Tyr Leu Thr Trp Val Pro Ala His Lys Gly
    530                 535                 540

Ile Gly Gly Asn Glu Lys Ile Asp Lys Leu Val Ser Lys Asp Ile Arg
545                 550                 555                 560

Arg Val Leu Glu Ser Thr His His His His His
                565                 570

<210> SEQ ID NO 12
<211> LENGTH: 1722
<212> TYPE: DNA
<213> ORGANISM: HIV-1 group O
<220> FEATURE:
<221> NAME/KEY: source
<222> LOCATION: 1..1722
<223> OTHER INFORMATION: /mol_type="unassigned DNA"
      /organism="HIV-1 group O"

<400> SEQUENCE: 12
atgaattctc ctataagccc catagcccca gtgccagtaa agctaaaacc aggaatggat      60
ggaccaaaag taaaacaatg gcccctatct aaagaaaaaa tagaagcctt aacagcaata     120
tgccaggaaa tggaacaaga aggaaaaatt tcaagaatag acctgaaaaa tccttataat     180
acacctatct ttgctataaa aaagaaagat agtactaagt ggagaaagct ggtagacttt     240
agggaattaa caagagaaac acaagatttt tgggaggtac agttaggtat cccacatccg     300
gggggtttaa agcaaaagcg atctgttaca gtcttagatg taggagatgc ctatttctca     360
tgccccttag acccagattt tagaaaatat actgctttca ctattcctag tgtaaacaat     420
gagaccccag gaataagata ccagtacaat gtcctcccgc aaggatggaa aggttcgcca     480
gccatattcc aaagttcaat gacaaaaatt ttagatccat ttaggaaaga aacccagaa     540 ttagaaattt gtcagtacat ggatgaccta tatgtaggat cagatttacc cctggcagaa     600
catagaaaaa gggttgaatt gcttagagaa cacttatatc agtggggatt cactacccct     660
gataaaaagc atcaaaagga acctcccttt atgtggatgg ggtatgagct ccatccagat     720
aaatggacag tacagcccat caaattgcct aacaaagatg tgtggacagt aaatgatata     780
caaaaactaa taggaaagtt aaattgggca agtcaaatct atcaaggaat tagagtaaga     840
gaattgtgta agttaattag aggcaccaag tcattaacag aagtagtacc attaagcaaa     900
gaggcagaga tggaattaga ggagaacaga gagaaattaa agaaccaat gcatggtgta     960 tactatcaac tgataaaaga cttatgggtt aatattcaga agcaaggaga agggcaatgg    1020
acttaccaga tatatcagga tgaacataag aacctcaaaa cagggaaata tactaggcaa    1080
aaggcctccc acacaaatga cataagacaa ttagcagaag taatccagaa ggtgtctcaa    1140
```

-continued

```
gaatctatag ttatctgggg aaaattgcct aaatttaagc tgccagtcac tagagaaact    1200
tgggaaacat ggtgggcaga ttattggcaa gccacctgga tcccagaatg ggattatgtc    1260
agcacacccc cattgatcaa attatggtac cggttagaaa gtgaacctat taggggggca    1320
gaaacctatt atgtagatgg agcagctaat agagatacaa aattaggaaa agcaggatat    1380
gttacagaac aagggaaaca gaaaataata aaattagatg agaccaccaa tcaaaaggct    1440
gaattaatgg cagtattatt agccttacag gattccaaag aaaaagtaaa tatagtaaca    1500
gactcacaat atgtattggg cattatctcc tcccagccta cacagagtga atcccctata    1560
gttcagcaga taatagagga actaacaaaa aaggaacagg tgtatcttac atgggttcct    1620
gctcataaag gcataggagg aaatgaaaaa atagataaat tagtaagcaa ggatattaga    1680
agagtcctcg agtcgactca ccaccaccac caccactgat aa                       1722
```

```
<210> SEQ ID NO 13
<211> LENGTH: 572
<212> TYPE: PRT
<213> ORGANISM: HIV-1 group O

<400> SEQUENCE: 13

Met Asn Ser Pro Ile Ser Pro Ile Ala Pro Val Pro Val Lys Leu Lys
1               5                   10                  15

Pro Gly Met Asp Gly Pro Lys Val Lys Gln Trp Pro Leu Ser Lys Glu
            20                  25                  30

Lys Ile Glu Ala Leu Thr Ala Ile Cys Gln Glu Met Glu Gln Glu Gly
        35                  40                  45

Lys Ile Ser Arg Ile Gly Pro Glu Asn Pro Tyr Asn Thr Pro Ile Phe
    50                  55                  60

Ala Ile Lys Lys Lys Asp Ser Thr Lys Trp Arg Lys Leu Val Asp Phe
65                  70                  75                  80

Arg Glu Leu Asn Lys Arg Thr Gln Asp Phe Trp Glu Val Gln Leu Gly
                85                  90                  95

Ile Pro His Pro Gly Gly Leu Lys Gln Lys Arg Ser Val Thr Val Leu
            100                 105                 110

Asp Val Gly Asp Ala Tyr Phe Ser Cys Pro Leu Asp Pro Asp Phe Arg
        115                 120                 125

Lys Tyr Thr Ala Phe Thr Ile Pro Ser Val Asn Asn Glu Thr Pro Gly
    130                 135                 140

Ile Arg Tyr Gln Tyr Asn Val Leu Pro Gln Gly Trp Lys Gly Ser Pro
145                 150                 155                 160

Ala Ile Phe Gln Ser Ser Met Thr Lys Ile Leu Asp Pro Phe Arg Lys
                165                 170                 175

Asp Asn Pro Glu Leu Glu Ile Cys Gln Tyr Met Asp Asp Leu Tyr Val
            180                 185                 190

Gly Ser Asp Leu Pro Leu Ala Glu His Arg Lys Arg Val Glu Leu Leu
        195                 200                 205

Arg Glu His Leu Tyr Gln Trp Gly Phe Thr Thr Pro Asp Lys Lys His
    210                 215                 220

Gln Lys Glu Pro Pro Phe Met Trp Met Gly Tyr Glu Leu His Pro Asp
225                 230                 235                 240

Lys Trp Thr Val Gln Pro Ile Lys Leu Pro Asn Lys Asp Val Trp Thr
                245                 250                 255

Val Asn Asp Ile Gln Lys Leu Ile Gly Lys Leu Asn Trp Ala Ser Gln
            260                 265                 270
```

Ile Tyr Gln Gly Ile Arg Val Arg Glu Leu Cys Lys Leu Ile Arg Gly
            275                 280                 285

Thr Lys Ser Leu Thr Glu Val Val Pro Leu Ser Lys Glu Ala Glu Met
        290                 295                 300

Glu Leu Glu Glu Asn Arg Glu Lys Leu Lys Glu Pro Met His Gly Val
305                 310                 315                 320

Tyr Tyr Gln Pro Asp Lys Asp Leu Trp Val Asn Ile Gln Lys Gln Gly
                325                 330                 335

Glu Gly Gln Trp Thr Tyr Gln Ile Tyr Gln Asp Glu His Lys Asn Leu
            340                 345                 350

Lys Thr Gly Lys Tyr Thr Arg Gln Arg Gly Ala His Thr Asn Asp Ile
        355                 360                 365

Arg Gln Leu Ala Glu Val Ile Gln Lys Val Ser Gln Glu Ser Ile Val
    370                 375                 380

Ile Trp Gly Lys Leu Pro Lys Phe Lys Leu Pro Val Thr Arg Glu Thr
385                 390                 395                 400

Trp Glu Thr Trp Trp Ala Asp Tyr Trp Gln Ala Thr Trp Ile Pro Glu
                405                 410                 415

Trp Asp Tyr Val Ser Thr Pro Pro Leu Ile Lys Leu Trp Tyr Arg Leu
            420                 425                 430

Glu Ser Glu Pro Ile Arg Gly Ala Glu Thr Tyr Tyr Val Asp Gly Ala
        435                 440                 445

Ala Asn Arg Asp Thr Lys Leu Gly Lys Ala Gly Tyr Val Thr Glu Gln
    450                 455                 460

Gly Lys Gln Lys Ile Ile Lys Leu Asp Glu Thr Thr Asn Gln Lys Ala
465                 470                 475                 480

Glu Leu Met Ala Val Leu Leu Ala Leu Gln Asp Ser Lys Glu Lys Val
                485                 490                 495

Asn Ile Val Thr Asp Ser Gln Tyr Val Leu Gly Ile Ile Ser Ser Gln
            500                 505                 510

Pro Thr Gln Ser Glu Ser Pro Ile Val Gln Gln Ile Ile Glu Glu Leu
        515                 520                 525

Thr Lys Lys Glu Gln Val Tyr Leu Thr Trp Val Pro Ala His Lys Gly
    530                 535                 540

Ile Gly Gly Asn Glu Lys Ile Asp Lys Leu Val Ser Lys Asp Ile Arg
545                 550                 555                 560

Arg Val Leu Glu Ser Thr His His His His His
                565                 570

<210> SEQ ID NO 14
<211> LENGTH: 1722
<212> TYPE: DNA
<213> ORGANISM: HIV-1 group O
<220> FEATURE:
<221> NAME/KEY: source
<222> LOCATION: 1..1722
<223> OTHER INFORMATION: /mol_type="unassigned DNA"
      /organism="HIV-1 group O"

<400> SEQUENCE: 14
atgaattctc ctataagccc catagcccca gtgccagtaa agctaaaacc aggaatggat      60
ggaccaaaag taaaacaatg gcccctatct aaagaaaaaa tagaagcctt aacagcaata     120
tgccaggaaa tggaacaaga aggaaaaatt tcaagaatag acctgaaaa tccttataat     180 acacctatct ttgctataaa aaagaaagat agtactaagt ggagaaagct ggtagacttt     240
agggaattaa acaagagaac acaagatttt tggggaggtac agttaggtat cccacatccg     300

```
ggggggtttaa agcaaaagcg atctgttaca gtcttagatg taggagatgc ctatttctca    360
tgccccttag acccagattt tagaaaatat actgctttca ctattcctag tgtaaacaat    420
gagaccccag gaataagata ccagtacaat gtcctcccgc aaggatggaa aggttcgcca    480
gccatattcc aaagttcaat gacaaaaatt ttagatccat ttaggaaaga acccagaa     540 ttagaaattt gtcagtacat ggatgaccta tatgtaggat cagatttacc cctggcagaa    600
catagaaaaa gggttgaatt gcttagagaa cacttatatc agtggggatt cactacccct    660
gataaaaagc atcaaaagga acctcccttt atgtggatgg ggtatgagct ccatccagat    720
aaatggacag tacagcccat caaattgcct aacaaagatg tgtggacagt aaatgatata    780
caaaaactaa taggaaagtt aaattgggca agtcaaatct atcaaggaat tagagtaaga    840
gaattgtgta agttaattag aggcaccaag tcattaacag aagtagtacc attaagcaaa    900
gaggcagaga tggaattaga ggagaacaga gagaaattaa agaaccaat gcatggtgta    960 tactatcaac ctgataaaga cttatgggtt aatattcaga agcaaggaga agggcaatgg    1020
acttaccaga tatatcagga tgaacataag aacctcaaaa cagggaaata tactaggcaa    1080
aggggcgccc acacaaatga cataagacaa ttagcagaag taatccagaa ggtgtctcaa    1140
gaatctatag ttatctgggg aaaattgcct aaatttaagc tgccagtcac tagagaaact    1200
tgggaaacat ggtgggcaga ttattggcaa gccacctgga tcccagaatg ggattatgtc    1260
agcacacccc cattgatcaa attatggtac cggttagaaa gtgaacctat tagggggggca    1320 gaaacctatt atgtagatgg agcagctaat agagatacaa aattaggaaa agcaggatat    1380
gttacagaac aagggaaaca gaaaataata aaattagatg agaccaccaa tcaaaaggct    1440
gaattaatgg cagtattatt agccttacag gattccaaag aaaagtaaa tatagtaaca    1500 gactcacaat atgtattggg cattatctcc tcccagccta cacagagtga atcccctata    1560
gttcagcaga taatagagga actaacaaaa aaggaacagg tgtatcttac atgggttcct    1620
gctcataaag gcataggagg aaatgaaaaa atagataaat tagtaagcaa ggatattaga    1680
agagtcctcg agtcgactca ccaccaccac caccactgat aa                       1722
```

<210> SEQ ID NO 15
<211> LENGTH: 572
<212> TYPE: PRT
<213> ORGANISM: HIV-1 group O

<400> SEQUENCE: 15

```
Met Asn Ser Pro Ile Ser Pro Ile Ala Pro Val Pro Val Lys Leu Lys
1               5                   10                  15

Pro Gly Met Asp Gly Pro Lys Val Lys Gln Trp Pro Leu Ser Lys Glu
            20                  25                  30

Lys Ile Glu Ala Leu Thr Ala Ile Cys Gln Glu Met Glu Gln Glu Gly
        35                  40                  45

Lys Ile Ser Arg Ile Gly Pro Glu Asn Pro Tyr Asn Thr Pro Ile Phe
    50                  55                  60

Ala Ile Lys Lys Lys Asp Ser Thr Lys Trp Arg Lys Leu Val Asp Phe
65                  70                  75                  80

Arg Glu Leu Asn Lys Arg Thr Gln Asp Phe Trp Glu Val Gln Leu Gly
                85                  90                  95

Ile Pro His Pro Gly Gly Leu Lys Gln Lys Arg Ser Val Thr Val Leu
            100                 105                 110

Asp Val Gly Asp Ala Tyr Phe Ser Cys Pro Leu Asp Pro Asp Phe Arg
```

-continued

```
            115                 120                 125
Lys Tyr Thr Ala Phe Thr Ile Pro Ser Val Asn Asn Glu Thr Pro Gly
130                 135                 140
Ile Arg Tyr Gln Tyr Asn Val Leu Pro Gln Gly Trp Lys Gly Ser Pro
145                 150                 155                 160
Ala Ile Phe Gln Ser Ser Met Thr Lys Ile Leu Asp Pro Phe Arg Lys
                165                 170                 175
Asp Asn Pro Glu Leu Glu Ile Cys Gln Tyr Met Asp Asp Leu Tyr Val
            180                 185                 190
Gly Ser Asp Leu Pro Leu Ala Glu His Arg Lys Arg Val Glu Leu Leu
        195                 200                 205
Arg Glu His Leu Tyr Gln Trp Gly Phe Thr Thr Pro Asp Lys Lys His
    210                 215                 220
Gln Lys Glu Pro Pro Phe Met Trp Met Gly Tyr Glu Leu His Pro Asp
225                 230                 235                 240
Lys Trp Thr Val Gln Pro Ile Lys Leu Pro Asn Lys Asp Val Trp Thr
                245                 250                 255
Val Asn Asp Ile Gln Lys Leu Ile Gly Lys Leu Asn Trp Ala Ser Gln
            260                 265                 270
Ile Tyr Gln Gly Ile Arg Val Arg Glu Leu Cys Lys Leu Ile Arg Gly
        275                 280                 285
Thr Lys Ser Leu Thr Glu Val Val Pro Leu Ser Lys Glu Ala Glu Met
    290                 295                 300
Glu Leu Glu Glu Asn Arg Glu Lys Leu Lys Glu Pro Met His Gly Val
305                 310                 315                 320
Tyr Tyr Gln Pro Asp Lys Asp Leu Trp Val Asn Ile Gln Lys Gln Gly
                325                 330                 335
Glu Gly Gln Trp Thr Tyr Gln Ile Tyr Gln Asp Glu His Lys Asn Leu
            340                 345                 350
Lys Thr Gly Lys Tyr Ala Arg Met Arg Gly Ala His Thr Asn Asp Ile
        355                 360                 365
Arg Gln Leu Ala Glu Val Ile Gln Lys Val Ser Gln Glu Ser Ile Val
    370                 375                 380
Ile Trp Gly Lys Leu Pro Lys Phe Lys Leu Pro Val Thr Arg Glu Thr
385                 390                 395                 400
Trp Glu Thr Trp Trp Ala Asp Tyr Trp Gln Ala Thr Trp Ile Pro Glu
                405                 410                 415
Trp Asp Tyr Val Ser Thr Pro Pro Leu Ile Lys Leu Trp Tyr Arg Leu
            420                 425                 430
Glu Ser Glu Pro Ile Arg Gly Ala Glu Thr Tyr Tyr Val Asp Gly Ala
        435                 440                 445
Ala Asn Arg Asp Thr Lys Leu Gly Lys Ala Gly Tyr Val Thr Glu Gln
    450                 455                 460
Gly Lys Gln Lys Ile Ile Lys Leu Asp Glu Thr Thr Asn Gln Lys Ala
465                 470                 475                 480
Glu Leu Met Ala Val Leu Leu Ala Leu Gln Asp Ser Lys Glu Lys Val
                485                 490                 495
Asn Ile Val Thr Asp Ser Gln Tyr Val Leu Gly Ile Ile Ser Ser Gln
            500                 505                 510
Pro Thr Gln Ser Glu Ser Pro Ile Val Gln Gln Ile Ile Glu Glu Leu
        515                 520                 525
Thr Lys Lys Glu Gln Val Tyr Leu Thr Trp Val Pro Ala His Lys Gly
    530                 535                 540
```

Ile Gly Gly Asn Glu Lys Ile Asp Lys Leu Val Ser Lys Asp Ile Arg
545                 550                 555                 560

Arg Val Leu Glu Ser Thr His His His His His His
                565                 570

<210> SEQ ID NO 16
<211> LENGTH: 1722
<212> TYPE: DNA
<213> ORGANISM: HIV-1 group O
<220> FEATURE:
<221> NAME/KEY: source
<222> LOCATION: 1..1722
<223> OTHER INFORMATION: /mol_type="unassigned DNA"
      /organism="HIV-1 group O"

<400> SEQUENCE: 16

| | | | | | | |
|---|---|---|---|---|---|---|
| atgaattctc | ctataagccc | catagcccca | gtgccagtaa | agctaaaacc | aggaatggat | 60 |
| ggaccaaaag | taaaacaatg | gcccctatct | aaagaaaaaa | tagaagcctt | aacagcaata | 120 |
| tgccaggaaa | tggaacaaga | aggaaaaatt | tcaagaatag | acctgaaaaa | tccttataat | 180 |
| acacctatct | ttgctataaa | aagaaagat | agtactaagt | ggagaaagct | ggtagacttt | 240 |
| agggaattaa | caagagaac | acaagatttt | tgggaggtac | agttaggtat | cccacatccg | 300 |
| gggggtttaa | agcaaaagcg | atctgttaca | gtcttagatg | taggagatgc | ctatttctca | 360 |
| tgccccttag | acccagattt | tagaaaatat | actgctttca | ctattcctag | tgtaaacaat | 420 |
| gagacccag | gaataagata | ccagtacaat | gtcctccgc | aaggatggaa | aggttcgcca | 480 |
| gccatattcc | aaagttcaat | gacaaaaatt | ttagatccat | ttaggaaaga | acccagaa | 540 |
| ttagaaattt | gtcagtacat | ggatgaccta | tatgtaggat | cagatttacc | cctggcagaa | 600 |
| catagaaaaa | gggttgaatt | gcttagagaa | cacttatatc | agtggggatt | cactacccct | 660 |
| gataaaaagc | atcaaaagga | acctccctt | atgtggatgg | ggtatgagct | ccatccagat | 720 |
| aaatggacag | tacagcccat | caaattgcct | aacaaagatg | tgtggacagt | aaatgatata | 780 |
| caaaaactaa | taggaaagtt | aaattgggca | agtcaaatct | atcaaggaat | tagagtaaga | 840 |
| gaattgtgta | agttaattag | aggcaccaag | tcattaacag | aagtagtacc | attaagcaaa | 900 |
| gaggcagaga | tggaattaga | ggagaacaga | gagaaattaa | agaaccaat | gcatggtgta | 960 |
| tactatcaac | ctgataaaga | cttatgggtt | aatattcaga | agcaaggaga | agggcaatgg | 1020 |
| acttaccaga | tatatcagga | tgaacataag | aacctcaaaa | cagggaaata | tgctaggatg | 1080 |
| aggggcgccc | acacaaatga | cataagacaa | ttagcagaag | taatccagaa | ggtgtctcaa | 1140 |
| gaatctatag | ttatctgggg | aaaattgcct | aaatttaagc | tgccagtcac | tagagaaact | 1200 |
| tgggaaacat | ggtgggcaga | ttattggcaa | gccacctgga | tcccagaatg | ggattatgtc | 1260 |
| agcacacccc | cattgatcaa | attatggtac | cggttagaaa | gtgaacctat | taggggggca | 1320 |
| gaaacctatt | atgtagatgg | agcagctaat | agagatacaa | aattaggaaa | agcaggatat | 1380 |
| gttacagaac | aagggaaaca | gaaaataata | aaattagatg | agaccaccaa | tcaaaaggct | 1440 |
| gaattaatgg | cagtattatt | agccttacag | gattccaaag | aaaaagtaaa | tatagtaaca | 1500 |
| gactcacaat | atgtattggg | cattatctcc | tcccagccta | cacagagtga | atcccctata | 1560 |
| gttcagcaga | taatagagga | actaacaaaa | aaggaacagg | tgtatcttac | atgggttcct | 1620 |
| gctcataaag | gcataggagg | aaatgaaaaa | atagataaat | tagtaagcaa | ggatattaga | 1680 |
| agagtcctcg | agtcgactca | ccaccaccac | caccactgat | aa | | 1722 |

```
<210> SEQ ID NO 17
<211> LENGTH: 574
<212> TYPE: PRT
<213> ORGANISM: HIV-1 group O

<400> SEQUENCE: 17

Met Asn Ser Pro Ile Ser Pro Ile Ala Pro Val Pro Val Lys Leu Lys
1               5                   10                  15

Pro Gly Met Asp Gly Pro Lys Val Lys Gln Trp Pro Leu Ser Lys Glu
            20                  25                  30

Lys Ile Glu Ala Leu Thr Ala Ile Cys Gln Glu Met Glu Gln Glu Gly
        35                  40                  45

Lys Ile Ser Arg Ile Gly Pro Glu Asn Pro Tyr Asn Thr Pro Ile Phe
    50                  55                  60

Ala Ile Lys Lys Lys Asp Ser Ser Ser Gly Lys Trp Arg Lys Leu Val
65                  70                  75                  80

Asp Phe Arg Glu Leu Asn Lys Arg Thr Gln Asp Phe Trp Glu Val Gln
                85                  90                  95

Leu Gly Ile Pro His Pro Gly Gly Leu Lys Gln Lys Arg Ser Val Thr
            100                 105                 110

Val Leu Asp Val Gly Asp Ala Tyr Phe Ser Cys Pro Leu Asp Pro Asp
        115                 120                 125

Phe Arg Lys Tyr Thr Ala Phe Thr Ile Pro Ser Val Asn Asn Glu Thr
    130                 135                 140

Pro Gly Ile Arg Tyr Gln Tyr Asn Val Leu Pro Gln Gly Trp Lys Gly
145                 150                 155                 160

Ser Pro Ala Ile Phe Gln Ser Ser Met Thr Lys Ile Leu Asp Pro Phe
                165                 170                 175

Arg Lys Asp Asn Pro Glu Leu Glu Ile Cys Gln Tyr Met Asp Asp Leu
            180                 185                 190

Tyr Val Gly Ser Asp Leu Pro Leu Ala Glu His Arg Lys Arg Val Glu
        195                 200                 205

Leu Leu Arg Glu His Leu Tyr Gln Trp Gly Phe Thr Thr Pro Asp Lys
    210                 215                 220

Lys His Gln Lys Glu Pro Pro Phe Met Trp Met Gly Tyr Glu Leu His
225                 230                 235                 240

Pro Asp Lys Trp Thr Val Gln Pro Ile Lys Leu Pro Asn Lys Asp Val
                245                 250                 255

Trp Thr Val Asn Asp Ile Gln Lys Leu Ile Gly Lys Leu Asn Trp Ala
            260                 265                 270

Ser Gln Ile Tyr Gln Gly Ile Arg Val Arg Glu Leu Cys Lys Leu Ile
    275                 280                 285

Arg Gly Thr Lys Ser Leu Thr Glu Val Val Pro Leu Ser Lys Glu Ala
290                 295                 300

Glu Met Glu Leu Glu Glu Asn Arg Glu Lys Leu Lys Glu Pro Met His
305                 310                 315                 320

Gly Val Tyr Tyr Gln Pro Asp Lys Asp Leu Trp Val Asn Ile Gln Lys
                325                 330                 335

Gln Gly Glu Gly Gln Trp Thr Tyr Gln Ile Tyr Gln Asp Glu His Lys
            340                 345                 350

Asn Leu Lys Thr Gly Lys Tyr Thr Arg Gln Arg Gly Ala His Thr Asn
        355                 360                 365

Asp Ile Arg Gln Leu Ala Glu Val Ile Gln Lys Val Ser Gln Glu Ser
    370                 375                 380
```

```
Ile Val Ile Trp Gly Lys Leu Pro Lys Phe Lys Leu Pro Val Thr Arg
385                 390                 395                 400

Glu Thr Trp Glu Thr Trp Trp Ala Asp Tyr Trp Gln Ala Thr Trp Ile
            405                 410                 415

Pro Glu Trp Asp Tyr Val Ser Thr Pro Pro Leu Ile Lys Leu Trp Tyr
            420                 425                 430

Arg Leu Glu Ser Glu Pro Ile Arg Gly Ala Glu Thr Tyr Tyr Val Asp
            435                 440                 445

Gly Ala Ala Asn Arg Asp Thr Lys Leu Gly Lys Ala Gly Tyr Val Thr
        450                 455                 460

Glu Gln Gly Lys Gln Lys Ile Ile Lys Leu Asp Glu Thr Thr Asn Gln
465                 470                 475                 480

Lys Ala Glu Leu Met Ala Val Leu Leu Ala Leu Gln Asp Ser Lys Glu
            485                 490                 495

Lys Val Asn Ile Val Thr Asp Ser Gln Tyr Val Leu Gly Ile Ile Ser
            500                 505                 510

Ser Gln Pro Thr Gln Ser Glu Ser Pro Ile Val Gln Gln Ile Ile Glu
        515                 520                 525

Glu Leu Thr Lys Lys Glu Gln Val Tyr Leu Thr Trp Val Pro Ala His
530                 535                 540

Lys Gly Ile Gly Gly Asn Glu Lys Ile Asp Lys Leu Val Ser Lys Asp
545                 550                 555                 560

Ile Arg Arg Val Leu Glu Ser Thr His His His His His His
            565                 570
```

<210> SEQ ID NO 18
<211> LENGTH: 1728
<212> TYPE: DNA
<213> ORGANISM: HIV-1 group O
<220> FEATURE:
<221> NAME/KEY: source
<222> LOCATION: 1..1728
<223> OTHER INFORMATION: /mol_type="unassigned DNA"
      /organism="HIV-1 group O"

<400> SEQUENCE: 18

```
atgaattctc ctataagccc catagcccca gtgccagtaa agctaaaacc aggaatggat      60
ggaccaaaag taaacaatg gcccctatct aaagaaaaaa tagaagcctt aacagcaata     120
tgccaggaaa tggaacaaga aggaaaaatt tcaagaatag acctgaaaaa tccttataat     180
acacctatct ttgctataaa aaagaaagat agtagttccg ggaagtggag aaagctggta     240
gactttaggg aattaaacaa gagaacacaa gattttttggg aggtacagtt aggtatccca     300
catccggggg gtttaaagca aaagcgatct gttacagtct tagatgtagg agatgcctat     360
ttctcatgcc cctagacccc agattttaga aaatatactg ctttcactat tcctagtgta     420
aacaatgaga ccccaggaat aagataccag tacaatgtcc tcccgcaagg atggaaaggt     480
tcgccagcca tattccaaag ttcaatgaca aaattttag atccatttag aaagacaac     540 ccagaattag aaatttgtca gtacatggat gacctatatg taggatcaga tttaccccctg     600 gcagaacata gaaaagggt tgaattgctt agagaacact tatatcagtg gggattcact     660 accccctgata aaaagcatca aaggaacct cccttttatgt ggatgggta tgagctccat     720 ccagataaat ggacagtaca gcccatcaaa ttgcctaaca aagatgtgtg gacagtaaat     780
gatatacaaa aactaatagg aaagttaaat tgggcaagtc aaatctatca aggaattaga     840
gtaagagaat tgtgtaagtt aattagaggc accaagtcat taacagaagt agtaccatta     900
```

-continued

```
agcaaagagg cagagatgga attagaggag aacagagaga aattaaaaga accaatgcat    960
ggtgtatact atcaacctga taaagactta tgggttaata ttcagaagca aggagaaggg   1020
caatggactt accagatata tcaggatgaa cataagaacc tcaaaacagg gaaatatact   1080
aggcaagggg cgcccacac aaatgacata agacaattag cagaagtaat ccagaaggtg    1140
tctcaagaat ctatagttat ctggggaaaa ttgcctaaat ttaagctgcc agtcactaga   1200
gaaacttggg aaacatggtg ggcagattat tggcaagcca cctggatccc agaatgggat   1260
tatgtcagca caccccatt gatcaaatta tggtaccggt tagaaagtga acctattagg    1320
ggggcagaaa cctattatgt agatggagca gctaatagag atacaaaatt aggaaaagca   1380
ggatatgtta cagaacaagg gaaacagaaa ataataaaat tagatgagac caccaatcaa   1440
aaggctgaat taatggcagt attattagcc ttacaggatt ccaaagaaaa agtaaatata   1500
gtaacagact cacaatatgt attgggcatt atctcctccc agcctacaca gagtgaatcc   1560
cctatagttc agcagataat agaggaacta acaaaaaagg aacaggtgta tcttacatgg   1620
gttcctgctc ataaaggcat aggaggaaat gaaaaaatag ataaattagt aagcaaggat   1680
attagaagag tcctcgagtc gactcaccac caccaccacc actgataa              1728
```

<210> SEQ ID NO 19
<211> LENGTH: 572
<212> TYPE: PRT
<213> ORGANISM: HIV-1 group O

<400> SEQUENCE: 19

```
Met Asn Ser Pro Ile Ser Pro Ile Ala Pro Val Pro Val Lys Leu Lys
 1               5                   10                  15

Pro Gly Met Asp Gly Pro Lys Val Lys Gln Trp Pro Leu Ser Lys Glu
            20                  25                  30

Lys Ile Glu Ala Leu Thr Ala Ile Cys Gln Glu Met Glu Gln Glu Gly
        35                  40                  45

Lys Ile Ser Arg Ile Gly Pro Glu Asn Pro Tyr Asn Thr Pro Ile Phe
    50                  55                  60

Ala Ile Lys Lys Lys Asp Ser Thr Lys Trp Arg Lys Leu Val Asp Phe
65                  70                  75                  80

Arg Glu Leu Asn Lys Arg Thr Gln Asp Phe Trp Glu Val Gln Leu Gly
                85                  90                  95

Ile Pro His Pro Gly Gly Leu Lys Gln Lys Arg Ser Val Thr Val Leu
            100                 105                 110

Asp Val Gly Asp Ala Tyr Phe Ser Cys Pro Leu Asp Pro Asp Phe Arg
        115                 120                 125

Lys Tyr Thr Ala Phe Thr Ile Pro Ser Val Asn Asn Glu Thr Pro Gly
    130                 135                 140

Ile Arg Tyr Gln Tyr Asn Val Leu Pro Gln Gly Trp Lys Gly Ser Pro
145                 150                 155                 160

Ala Ile Phe Gln Ser Ser Met Thr Lys Ile Leu Asp Pro Phe Arg Lys
                165                 170                 175

Asp Asn Pro Glu Leu Glu Ile Cys Gln Tyr Met Asp Asp Leu Tyr Val
            180                 185                 190

Gly Ser Asp Leu Pro Leu Ala Glu His Arg Lys Arg Val Glu Leu Leu
        195                 200                 205

Arg Glu His Leu Tyr Gln Trp Gly Phe Thr Thr Pro Asp Lys Lys His
    210                 215                 220

Gln Lys Glu Pro Pro Phe Met Trp Met Gly Tyr Glu Leu His Pro Asp
```

```
                225                 230                 235                 240
Lys Trp Thr Val Gln Pro Ile Lys Leu Pro Asn Lys Asp Val Trp Thr
                    245                 250                 255

Val Asn Asp Ile Gln Lys Leu Ile Gly Lys Leu Asn Trp Ala Ser Gln
                260                 265                 270

Ile Tyr Gln Gly Ile Arg Val Arg Glu Leu Cys Lys Leu Ile Arg Gly
                275                 280                 285

Thr Lys Ser Leu Thr Glu Val Val Pro Leu Ser Lys Glu Ala Glu Met
            290                 295                 300

Glu Leu Glu Glu Asn Arg Glu Lys Leu Lys Glu Pro Met His Gly Val
305                 310                 315                 320

Tyr Tyr Gln Pro Asp Lys Asp Leu Trp Val Asn Ile Gln Lys Gln Gly
                    325                 330                 335

Glu Gly Gln Trp Thr Tyr Gln Ile Tyr Gln Asp Glu His Lys Asn Leu
                340                 345                 350

Lys Thr Gly Lys Tyr Thr Arg Gln Arg Gly Ala His Thr Asn Asp Ile
                355                 360                 365

Arg Gln Leu Ala Glu Val Ile Gln Lys Val Ser Gln Glu Ser Ile Val
            370                 375                 380

Ile Trp Gly Lys Leu Pro Lys Phe Lys Leu Pro Val Thr Arg Glu Thr
385                 390                 395                 400

Trp Glu Thr Trp Trp Ala Asp Tyr Trp Gln Ala Thr Trp Ile Pro Glu
                    405                 410                 415

Trp Asp Tyr Val Ser Thr Pro Pro Leu Ile Lys Leu Trp Tyr Arg Leu
                420                 425                 430

Glu Ser Glu Pro Ile Arg Gly Ala Glu Thr Tyr Tyr Val Asp Gly Ala
            435                 440                 445

Ala Asn Arg Asp Thr Lys Leu Gly Lys Ala Gly Tyr Val Thr Glu Gln
                450                 455                 460

Gly Lys Gln Lys Ile Ile Lys Leu Asp Glu Thr Thr Asn Gln Lys Ala
465                 470                 475                 480

Gln Leu Met Ala Val Leu Leu Ala Leu Gln Asp Ser Lys Glu Lys Val
                    485                 490                 495

Asn Ile Val Thr Asp Ser Gln Tyr Val Leu Gly Ile Ile Ser Ser Gln
                500                 505                 510

Pro Thr Gln Ser Glu Ser Pro Ile Val Gln Ile Ile Glu Glu Leu
            515                 520                 525

Thr Lys Lys Glu Gln Val Tyr Leu Thr Trp Val Pro Ala His Lys Gly
530                 535                 540

Ile Gly Gly Asn Glu Lys Ile Asp Lys Leu Val Ser Lys Asp Ile Arg
545                 550                 555                 560

Arg Val Leu Glu Ser Thr His His His His His
                    565                 570

<210> SEQ ID NO 20
<211> LENGTH: 1722
<212> TYPE: DNA
<213> ORGANISM: HIV-1 group O
<220> FEATURE:
<221> NAME/KEY: source
<222> LOCATION: 1..1722
<223> OTHER INFORMATION: /mol_type="unassigned DNA"
      /organism="HIV-1 group O"

<400> SEQUENCE: 20
atgaattctc ctataagccc catagcccca gtgccagtaa agctaaaacc aggaatggat      60
```

```
ggaccaaaag taaaacaatg gcccctatct aaagaaaaaa tagaagcctt aacagcaata      120
tgccaggaaa tggaacaaga aggaaaaatt tcaagaatag gacctgaaaa tccttataat      180
acacctatct ttgctataaa aagaaagat agtactaagt ggagaaagct ggtagacttt       240
agggaattaa acaagagaac acaagatttt tgggaggtac agttaggtat cccacatccg      300
gggggtttaa agcaaaagcg atctgttaca gtcttagatg taggagatgc ctatttctca      360
tgccccttag acccagattt tagaaaatat actgctttca ctattcctag tgtaaacaat     420
gagaccccag gaataagata ccagtacaat gtcctcccgc aaggatggaa aggttcgcca    480
gccatattcc aaagttcaat gacaaaaatt ttagatccat ttaggaaaga caacccagaa    540
ttagaaattt gtcagtacat ggatgaccta tatgtaggat cagatttacc cctggcagaa    600
catagaaaaa gggttgaatt gcttagagaa cacttatatc agtggggatt cactacccct    660
gataaaaagc atcaaaagga acctcccttt atgtggatgg ggtatgagct ccatccagat    720
aaatggacag tacagcccat caaattgcct aacaaagatg tgtggacagt aaatgatata    780
caaaaactaa taggaaagtt aaattgggca agtcaaatct atcaaggaat tagagtaaga    840
gaattgtgta agttaattag aggcaccaag tcattaacag aagtagtacc attaagcaaa    900
gaggcagaga tggaattaga ggagaacaga gagaaattaa aagaaccaat gcatggtgta   960
tactatcaac ctgataaaga cttatgggtt aatattcaga agcaaggaga agggcaatgg   1020
acttaccaga tatatcagga tgaacataag aacctcaaaa cagggaaata tactaggcaa    1080
aggggcgccc acacaaatga cataagacaa ttagcagaag taatccagaa ggtgtctcaa   1140
gaatctatag ttatctgggg aaaattgcct aaatttaagc tgccagtcac tagagaaact   1200
tgggaaacat ggtgggcaga ttattggcaa gccacctgga tcccagaatg ggattatgtc   1260
agcacacccc cattgatcaa attatggtac cggttagaaa gtgaacctat taggggggca   1320
gaaacctatt atgtagatgg agcagctaat agagatacaa aattaggaaa agcaggatat   1380
gttacagaac aagggaaaca gaaaataata aaattagatg agaccaccaa tcaaaaggct   1440
caattaatgg cagtattatt agccttacag gattccaaag aaaaagtaaa tatagtaaca   1500
gactcacaat atgtattggg cattatctcc tcccagccta cacagagtga atcccctata   1560
gttcagcaga taatagagga actaacaaaa aaggaacagg tgtatcttac atgggttcct   1620
gctcataaag gcataggagg aaatgaaaaa atagataaat tagtaagcaa ggatattaga   1680
agagtcctcg agtcgactca ccaccaccac caccactgat aa                       1722
```

HIV TYPE 1 GROUP O REVERSE TRANSCRIPTASES THAT ARE ACTIVE AT HIGH TEMPERATURES

CROSS-REFERENCE TO RELATED APPLICATIONS

The present patent application is a national phase application of International Application No. PCT/ES2014/070389, filed May 8, 2014, which claims priority to Spanish Application No. P201330705, filed May 17, 2013, the disclosures of which are incorporated herein by reference.

This invention is in the field of biotechnology. More specifically it refers to reverse transcriptases expressed and purified in bacteria and that have the amino acid sequence of the reverse transcriptase of human immunodeficiency virus type 1 group O (HIV-1) modified in various positions. These polymerases have higher activity than the non-mutated enzyme at elevated temperatures (above 60° C.). They also retain DNA synthesis ability at temperatures of over 70° C. The copying fidelity of these enzymes does not significantly differ from that of the non-mutated reverse transcriptase.

STATE OF THE ART

In retroviruses, reverse transcriptase (RT) is the enzyme responsible for replicating the viral genome. RT converts the single-stranded RNA genome into double-stranded DNA capable of integration into the genome of the host cell [reviewed by Le Grice. *J Biol Chem*, 2012; 287: 40850-40857]. This is a polymerase that can synthesise DNA using either RNA or DNA as the template. RT also has endonuclease activity (ribonuclease H), which enables it to degrade the RNA template during RNA-dependent DNA synthesis process.

Retroviral RTs are useful enzymes for obtaining complementary DNA (cDNA) from messenger RNA (mRNA) or micro RNAs (miRNA), which when amplified by conventional techniques (for example PCR) can be used for detecting gene expression in organisms or tissues. RT efficiency is important in many biotechnological applications. For example, for the detection of mRNAs, quantification by real time PCR, analysis of gene expression using "microarrays" and also in transcriptomic studies using massive sequencing techniques. However, the presence of secondary structures in the RNA can reduce the effectiveness of these techniques. Having RTs available that are capable of synthesising DNA at elevated temperatures would be useful for improving the yield in amplification processes.

From a methodological point of view, the RTs most often used commercially in amplification reactions are those of the avian myeloblastosis virus (AMV), Moloney Murine Leukaemia Virus (MLV) (Coté and Roth. *Virus Res* 2008; 134: 186-202) and variants of the RT of the human immunodeficiency virus type 1 (HIV-1) (reviewed in Hizi and Herschhorn. *Virus Res* 2008; 134: 203-220). The AMV and MLV RTs are the most commonly used in RT-PCR assays, although that of AMV has better thermal stability at temperatures in the range of 42 to 52° C. (Gerard et al. *Nucleic Acids Res*. 2002; 30: 3118-3129). There are variants of MLV RT such as AffinityScript (Agilent) or Super Script III (Invitrogen) that are marketed as enzymes active at higher temperatures (Arezi and Hogrefe. *Nucleic Acids Res*. 2009; 37: 473-481).

Studies performed with HIV-1 RTs, classified as belonging to group M (subtype B), have demonstrated that these enzymes have higher activity and thermal stability than the MLV RT, although they are exceeded by a "wild type" RT variant derived from a HIV-1 that is phylogenetically distinct and classified as belonging to group O (Álvarez et al. *J Mol Biol* 2009; 392: 872-884; patent WO2010130864 (A1)). In RT-PCR assays applied to the expression of tubulin messenger RNA, the MLV RT did not give rise to amplification at temperatures exceeding 52° C., although "wild-type" RTs of group O or of subtype B were active at temperatures of up to 64° C., although only the first of these amplified at 66-68° C. (Álvarez et al. *J Mol Biol* 2009; 392: 872-884). HIV-1 RTs are heterodimers composed of two subunits, one of 560 amino acids (known as p66) and the other of 440 amino acids (known as p51). The sequence of p51 is identical to that of amino acids 1-440 of p66. The HIV-1 group O RTs are characterised by showing about 20% amino acid sequence differences when compared with the "wild-type" prototype of subtype B (Quiñones-Mateu et al. *Virology* 1997; 236: 364-373). Various RTs of group O have been characterised as having higher copying fidelity than the "wild-type" RT such as, for example, the carriers of the mutations V75I, K65R and K65R/V75I. These RTs have thermal stability and catalytic efficiencies at elevated temperatures similar to those shown by the "wild-type" RT (Barrioluengo et al. *Biochem J* 2011; 436: 599-607; patent WO2012080541 (A1)).

DESCRIPTION OF THE INVENTION

Brief Description

This invention refers to reverse transcriptases isolated from a human immunodeficiency virus type 1 group O (HIV-1) and modified in one or more positions that have higher thermostability than the original enzyme, maintaining copying fidelity, as well as their use for performing reverse transcription, amplification or sequencing of a nucleic acid template.

A first object of the invention refers to the polypeptide that codes for a protein with RT activity isolated from a HIV-1 group O and that has higher stability at high temperatures, and that has higher activity than the WT enzyme at temperatures over 75° C., maintaining copying fidelity, and characterised by its amino acid sequence that is at least 50% identical to the parent sequence SEQ ID NO 1 and in that it comprises alterations in its amino acid sequence (such as, for example, substitutions, deletions and/or insertions) in the following positions:

the position homologous to position 358 of this sequence, which replaces the original amino acid lysine (K) with the amino acid arginine (R) (mutation K358R)

the position homologous to position 359 of this sequence, which replaces original amino acid alanine (A) with the amino acid glycine (G) (mutation A359G)

the position homologous to position 360 of this sequence, which replaces original amino acid serine (S) with amino acid alanine (A) (mutation S360A).

Other reverse transcriptase variants are also described that contain additional changes to the combination K358R/A359G/S360A (common to all) and that improve the thermostability of the WT RT, that is their ability to synthesise DNA at elevated temperatures using RNA as a template. These amino acid changes and insertions belong, by way of illustration and without limiting the scope of the invention, to the following group:

a) Replacement of amino acid threonine (T) by the insertion of two amino acids serine and glycine (SSG) in the position homologous to position 69 of SEQ ID NO 1 (mutation T69SSG)
b) Replacement of amino acid threonine (T) by the amino acid alanine (A) in the position homologous to position 355 of the SEQ ID NO 1 (mutation T355A)
c) Replacement of amino acid glutamine (Q) by amino acid methionine (M) in the position homologous to position 357 of SEQ ID NO 1 (mutation Q357M)
d) Replacement of glutamic acid (E) by amino acid glutamine (Q) in the position homologous to position 478 of SEQ ID NO 1 (E478Q).

This invention includes, as a particular object of the invention, various variants of the HIV-1 of group O reverse transcriptase that have been used as a starting point and that have the mutations previously described, and where the particular polypeptide sequences correspond to SEQ ID NO 3, SEQ ID NO 5, SEQ ID NO 7 and SEQ ID NO 9; as well as their corresponding nucleotide sequences (SEQ ID NO 4, SEQ ID NO 6, SEQ ID NO 8, SEQ ID NO 10).

Another object of the invention are the vectors comprising polynucleotides that code for the reverse transcriptases of the invention.

Another object of the invention is the cell that comprises the polynucleotide that codes for the reverse transcriptases of the invention. Preferably this cell is a bacterium, and more preferably still it is *Escherichia coli.*

Another object of this invention is the method of obtaining the polypeptide of the invention that comprises the following steps:

1) Introducing the vector of the invention into a suitable host cell (host cell of the invention)
2) Cultivating the host cell of the invention in a suitable medium, and
3) Purifying the polypeptide of the invention with RT activity.

Another object of the invention refers to the use of the polynucleotide of the invention to obtain the polypeptide of the invention with reverse transcriptase activity.

Another object of the invention refers to the use of the host cell of the invention to obtain the polypeptide of the invention.

Another object of the invention is the use of the polypeptide of the invention in methods of reverse transcription, amplification and sequencing of nucleic acids. Preferably, mRNA.

Another object of the invention refers to a kit that comprises the necessary components to carry out each of the methods described in this description and that preferably comprises:

a) the RT of the invention, and
b) at least one component of the list comprising:
   i) a buffer
   ii) a primer
   iii) a DNA-dependent DNA polymerase, and
   iv) a nucleotide.

DETAILED DESCRIPTION

Reverse transcriptases (RTs) of retroviruses are useful enzymes, for example for obtaining complementary DNA from messenger RNA, which when amplified can be cloned in a vector. It is desirable that the RTs that are used for this purpose have high thermal stability, because in these conditions the levels of secondary structure in the RNA are reduced and this improves the amplification process. However, RTs are enzymes that lack proofreading exonuclease activity and therefore have a relatively high error rate; so an increase in copying fidelity would be desirable for them to be used for this purpose.

Starting from the existence of sequence homologies between the RTs of HIV-1 group M subtype B (for example BH10 or HXB2) and the RTs of group O, the inventors have constructed a molecular model of the latter bound to a template-primer complex, based on the crystallographic structure deposited in the Protein Data Bank, as file 1RTD (www.pdb.org). This structure is the only one available in which a RT of HIV-1 (in this case of the strain HXB2) appears forming a ternary complex with double-stranded DNA (template-primer) and an incoming nucleotide (dTTP in this case). This is also a complete structure and with good resolution. Starting from the molecular model based on sequence homology, key positions were identified in the interaction with the template-primer in both enzymes. This information was used to design variants of the RT of group O (RTO) with higher affinity for nucleic acids. Thus by site-directed mutagenesis, the inventors obtained four new variants of the HIV-1 group O RT, designated as RTO_3M, RTO_5M, RTO_T69SSG_3M, RTO_E478Q_3M that contained mutations K358R/A359G/S360A, T355A/Q357M/K358R/A359G/S360A, T69SSG/K358R/A359G/S360A and K358R/A359G/S360A/E478Q respectively.

These enzymes were expressed in *Escherichia coli* and purified for subsequent characterisation, following a procedure similar to that described in WO2010130864. It was observed that in comparison to the "wild-type" RT of group O (RTO_WT), the four enzymes have higher DNA polymerase activity at temperatures exceeding 75° C. in RNA amplification reactions by RT-PCR, both in quantitative (FIG. 1) and in qualitative (FIG. 2) assays. The fidelity assays carried out with these enzymes demonstrated that their copying fidelity is maintained with respect to that of the RTO_WT (Tables 2 and 3; FIG. 3).

This invention refers to RTs isolated from a human immunodeficiency virus of type 1 group O (HIV-1) and modified in one or more positions that have higher thermostability than the WT enzyme, maintaining copying fidelity, as well as its use to carry out reverse transcription, amplification or sequencing of a template nucleic acid.

The starting point was a RT identified in a patient who had not been treated with antiretroviral drugs and who was infected by HIV-1 group O (strain ESP49) (Quiñones-Mateu et al. *Virology* 1997; 236: 364-373; Menéndez-Arias et al. *J. Biol. Chem.* 2001; 276: 27470-27479) (RTO_WT with polypeptide sequence SEQ ID NO 1). The nucleotide sequence of the p66 subunit of this RT was cloned into an expression vector that contained suitable restriction sites and a histidine tail at the C-terminal end followed by a termination codon in order to obtain and purify the enzyme (Álvarez et al. *J Mol Biol* 2009; 392: 872-884) (with nucleotide sequence SEQ ID NO 2). Using this construction and after a site-directed mutagenesis process, 4 variants were obtained that showed higher thermostability in comparison with the starting enzyme (RTO_WT) and that maintained copying fidelity. This adaptation of the RTs is potentially useful for the amplification of difficult RNAs, that is, those containing secondary structures and/or sequences rich in G:C base pairs.

A summary of the polynucleotide and polypeptide sequences described in this invention is shown in Table 1.

| Name | Mutations | Polypeptide | Nucleotide |
|---|---|---|---|
| RTO_WT | | SEQ ID NO 1 | SEQ ID, NO 2 |
| RTO_3M | K358R/A359G/S360A | SEQ ID NO 3 | SEQ ID NO 4 |
| RTO_5M | T355A/Q357M/ K358R/A359G/S360A | SEQ ID NO 5 | SEQ ID NO 6 |
| RTO_T69SSG_3M | T69SSG/K358R/ A359G/S360A | SEQ ID NO 7 | SEQ ID NO 8 |
| RTO_E478Q_3M | K358R/A359G/ S360A/E478Q | SEQ ID NO 9 | SEQ ID NO 10 |
| RTO_WT* | | SEQ ID NO 11 | SEQ ID NO 12 |
| RTO_3M* | K358R/A359G/S360A | SEQ ID NO 13 | SEQ ID NO 14 |
| RTO_5M* | T355A/Q357M/ K358R/A359G/S360A | SEQ ID NO 15 | SEQ ID NO 16 |
| RTO_T69SSG_3M* | T69SSG/K358R/ A359G/S360A | SEQ ID NO 17 | SEQ ID NO 18 |
| RTO_E478Q_3M* | K358R/A359G/ S360A/E478Q | SEQ ID NO 19 | SEQ ID NO 20 |

Therefore, a first object of the invention refers to the polypeptide that codes for a protein with RT activity isolated from HIV-1 group O and that has higher stability at high temperatures, hereafter the polypeptide of the invention, and that has higher activity than the WT enzyme at temperatures exceeding 75° C., maintaining its copying fidelity, and characterised in that its amino acid sequence is at least 50% identical to parental sequence SEQ ID NO 1, and in that it comprises alterations in its amino acid sequence (such as, for example, substitutions, deletions and/or insertions) in the following positions:
  the position homologous to position 358 of this sequence, which replaces the original amino acid lysine (K) with the amino acid arginine (R) (mutation K358R)
  the position homologous to position 359 of this sequence, which replaces original amino acid alanine (A) with the amino acid glycine (G) (mutation A359G)
  the position homologous to position 360 of this sequence, which replaces original amino acid serine (S) with amino acid alanine (A) (mutation S360A).

Thus in a preferred object of the invention, the substitutions in the polypeptide of the invention are K358R, A359G and S360A (reverse transcriptase RTO_3M). In a particular embodiment of the invention, the polypeptide of the invention corresponds to SEQ ID NO 3.

The temperature at which the RT has maximum DNA polymerase activity (depending on RNA or on DNA) is called the optimum temperature. Above this temperature, catalytic activity decreases, partly due to thermal denaturation of the RT. The term "thermostability" refers to the stability showed by a RT when it is subjected to an elevated temperature, for example, typically to a temperature of at least 50° C., preferably of at least 63° C., more preferably of at least 68° C. and still more preferably of at least 75° C.

The thermostability of the RT of the invention can be determined by different types of assay. It can be estimated, for example but without limitation, by analysing the amount of product obtained during the synthesis of DNA using a messenger RNA template in a RT-PCR, that may be qualitative or quantitative. To do this, a first reaction of the reverse transcriptase is performed at an elevated temperature, and then the complementary DNA obtained is amplified by PCR. The amount of product obtained after these reactions constitutes a measurement of the stability of the RT at the temperature at which the reverse transcriptase reaction was carried out. The analysis of the product in agarose gels enables a qualitative evaluation of the effectiveness of the reaction. Similarly, the yield of the reverse transcription stage can be determined by real time PCR determining the value of $\Delta Ct$, as $\Delta Ct = Ct - Ct(ref)$, where Ct is the cycle in which significant amplification is observed and Ct(ref) is the mean of the Ct values obtained for a RT used as reference.

A "synthesis reaction at elevated temperature", as used in this description, refers to a reaction, and more preferably a reverse transcription reaction, that is performed at a temperature of at least 50° C., preferably of at least 63° C., more preferably of at least 68° C., more preferably of at least 75° C., and still more preferably of at least 78° C.

A RT with "increased" or "augmented" thermostability is defined as a RT that has an significantly increased or augmented thermostability (applying statistical criteria) of at least 1.5 times, more preferably at least 2 times, and still more preferably of at least 3 times, and still more preferably of at least 4 times that of the RT with which the comparison is made.

The term "copying fidelity" refers to the accuracy of the DNA polymerisation process catalysed by the RT, which is influenced by its ability to discriminate between correct and incorrect substrates, either nucleotides or template-primer complexes, during the synthesis of complementary DNA to a nucleic acid that serves as a template.

The fidelity of the RT of this invention can be analysed by various types of assays such as, for example but without limitation, fidelity assays in cell cultures or "in vitro" fidelity assays (genetic or biochemical).

In biochemical assays, purified RT is used for the determination of kinetic constants on a RNA or DNA template under specified conditions (pH, substrate concentration, etc.). In this way, the kinetic parameters of fidelity of DNA synthesis (RNA- or DNA-dependent) of the RT can be obtained, both in steady state and pre-steady state. The biochemical assays for incorrect incorporation in steady state are based on the determination of the kinetic constants ($k_{cat}$ and $K_m$) for the incorporation of nucleotides at the 3' end of a primer and provide an estimate of the selectivity of the RT for the nucleotide. The determination of kinetic parameters is carried out by measuring nucleotide incorporation at the 3' end of the primer, previously labelled at their 5' end with [$\gamma^{32}$P]ATP, in the presence of different concentrations of dNTP, after forming the RT/template-primer binary complex. The resulting products are analysed by electrophoresis on polyacrylamide gels. The data obtained fitted to the Michaelis-Menten equation and the parameters $k_{cat}$ (rate of incorporation) and $K_m$ (Michaelis-Menten constant) are determined for the correct and incorrect nucleotides. The misincorporation efficiency ($f_{inc}$) is defined as the ratio between the catalytic efficiencies ($k_{cat}/K_m$) obtained for the incorrect nucleotide and the catalytic efficiencies obtained for the correct nucleotide. Thus, higher fidelity of the RT implies less efficiency of erroneous incorporation.

In order for the error in the nascent DNA to be fixed, incorporation of an incorrect nucleotide is not sufficient; the RT must be also able to extend the mispaired end that is generated as a consequence of this erroneous incorporation. This fidelity measurement is performed by mispair extension assays. In these assays, the kinetic constants in the steady state for the incorporation of a correct nucleotide on two types of template-primer complexes are calculated: the complex with the 3' end correctly paired and the same complex with the 3' end mispaired. The mispair extension efficiency ($f_{ext}$) is defined as the ratio between $k_{cat}/K_m$ obtained for the extension of the mispaired end and that obtained for the extension of the correctly paired end.

Biochemical assays in the pre-steady state asses the ability of the RT to bind and incorporate the dNTP at short time scales (such as for example in the order of milliseconds). In this way it is possible to calculate the affinity constant ($K_d$) for the interaction between the dNTP and the RT/template-primer binary complex and the polymerisation constant ($k_{pol}$). The efficiency of erroneous incorporation and of extension of the mispaired ends is determined from the values of $k_{pol}/K_d$ obtained for the incorporation of correct and incorrect nucleotides, or those obtained for the incorporation of correct nucleotides on template-primer complexes that contain a paired or mispaired 3'-OH ends.

The most commonly used genetic assays, named "forward mutation assays", are often carried out using the double-stranded DNA of the M13mp2 phage as the template-primer of the DNA synthesis reaction after first removing the sequence corresponding to the lacZ gene from one of the strands. The DNA synthesis reaction is carried out in the presence of the RT and of high concentrations of dNTPs. After bacterial transformation with the reaction product, mutants are identified as blue/white plaques in culture medium containing X-Gal (5-bromo-4-chloro-3-indolyl-β-D-galactopyranoside) and IPTG (Isopropyl β-D-1-thiogalactopyranoside). In this way, if there are no errors in the DNA synthesis reaction, the result is a dark blue plaque. By contrast, the introduction of one or more errors implies partial or total loss of the α-complementation, which results in light blue or white plaques. The DNA recovered from these plaques can be sequenced to determine exactly the number, type and position in the genome of the mutations introduced by the RT.

A RT with "increased" or "augmented" copying fidelity is defined as a RT that has an increase or a significant increase (applying statistical criteria) in copying fidelity compared to non-modified RT, typically of at least 1.5 times, more preferably of at least 2 times, and still more preferably of at least 3 times, and still more preferably of at least 4 times. For example, in biochemical assays of nucleotide incorporation, an increase in fidelity is considered when the value obtained for the modified RT is significantly greater than that of the non-modified RT (applying statistical criteria), typically of at least 1.5 times, more preferably of at least 2 times, and still more preferably of at least 3 times, and still more preferably of at least 4 times. For example in genetic assays ("forward mutation assays") increased fidelity is when there is a significant increase (applying statistical criteria) in the frequency of mutation obtained by the modified RT of typically at least 50% (1.5 times), preferably of at least 2 times, more preferably of at least 3 times and still more preferably of at least 4 times.

Along with the RT carrying the changes K358R, A359G and S360A, RTO_3M, other variants of HIV-1 group O RT are described that contain changes in addition to the K358R/A359G/S360A combination (common to all) and that improve the thermostability of the WT RT, that is, its ability to synthesise DNA at elevated temperatures using RNA as template. These amino acid changes and insertions belong, by way of illustration and without limiting the scope of the invention, to the following group:

e) Replacement of amino acid threonine (T) by the insertion of two amino acids serine and glycine (SSG) in the position homologous to position 69 of SEQ ID NO 1 (mutation T69SSG)

f) Replacement of amino acid threonine (T) by the amino acid alanine (A) in the position homologous to position 355 of the SEQ ID NO 1 (mutation T355A)

g) Replacement of amino acid glutamine (Q) by amino acid methionine (M) in the position homologous to position 357 of SEQ ID NO 1 (mutation Q357M)

h) Replacement of glutamic acid (E) by amino acid glutamine (Q) in the position homologous to position 478 of SEQ ID NO 1 (E478Q).

Thus, in another preferred object of the invention, the polypeptide of the invention has changes in amino acids K358R/A359G/S360A and also substitutions T355A and Q357M (reverse transcriptase RTO_5M). In a particular embodiment, the polypeptide of the invention corresponds to SEQ ID NO 5.

In another preferred object of the invention, the polypeptide of the invention has changes in amino acids K358R/A359G/S360A and also T69SSG (reverse transcriptase RTO_T69SSG_3M). In a particular embodiment, the polypeptide of the invention corresponds to SEQ ID NO 7.

In another preferred object of the invention, the polypeptide of the invention has changes in amino acids K358R/A359G/S360A and also the replacement E478Q (reverse transcriptase RTO_E478Q_3M). In a particular embodiment, the polypeptide of the invention corresponds to SEQ ID NO 9.

Additionally, the polypeptide of the invention can be flanked by small polypeptide fragments, the presence of which is necessary and/or beneficial for the expression of the polypeptide in a suitable vector, and that are known in the state of the art. Among these there are three amino acids at the N-terminal end (MNS, that is methionine-asparagine-serine), this sequence being included to facilitate the initiation of translation and to accommodate restriction endonuclease recognition sites, useful for constructing expression vectors that contain the reverse transcriptase. Also included here there are sequences that enable an improvement in the purification of the polypeptide such as a tail of histidine residues at the C-terminal end, when this preferably consists of at least 6 histidine residues. The flanking residues of the polypeptide of the invention give rise to new polypeptide sequences that contain the polypeptide of the invention and that maintain its reverse transcriptase activity.

Thus, in another preferred object of the invention, the reverse transcriptases RTO_3M, RTO_5M, RTO_T69SSG_3M and RTO_E478Q_3M have MNS flanking sequences at the N-terminal end and a histidine tail at the C-terminal, giving rise to polypeptides with reverse transcriptase activity: RTO_3M*, RTO_5M*, RTO_T69SSG_3M* and RTO_E478Q_3M*, that in a particular object correspond to, respectively, the polypeptide sequences SEQ ID NO 13, SEQ ID NO 15, SEQ ID NO 17 and SEQ ID NO 19.

The mutations described here introduced in the "wild-type" polypeptide sequence of a RT isolated from a HIV-1 group O can be obtained by genetic engineering or recombinant DNA techniques such as for example, mutating the sequence coding for the RT by site-directed mutagenesis or at random, or can be obtained by chemical synthesis of the nucleotide sequence that codes for the p66 subunit of the RT bearing the mutations.

As used in this description, the term "mutation" refers to a substitution of one amino acid by another different amino acid. Individual amino acids in a sequence are represented here as XN, in which X is the amino acid in the sequence (designed by the universally accepted one letter code for the nomenclature of amino acids) and N is the position in the sequence. Substitution point mutations in an amino acid sequence are represented here as X1NX2, in which X1 is the amino acid in the non-mutated protein sequence, X2 is/are the new amino acid/s of the mutated protein sequence and N is the position in the amino acid sequence.

Furthermore, with the information supplied, an expert in the field would be able to combine the mutations mentioned above in this invention to generate new RT variants with similar or improved activity at elevated temperatures. One possibility is the conservative substitution of the amino acids in the positions previously mentioned. Thus, for example, a conservative substitution is one that maintains the characteristics of polarity and charge of the substituted amino acid. For example, lysine and arginine are amino acids where the side chains are positively charged at neutral pH, so changes of lysine by arginine or vice versa represent conservative changes. The 20 amino acids that constitute the base of all natural proteins have been classified in accordance with their conservativeness into groups: (i) aromatic amino acids (phenylalanine, tyrosine, tryptophan); (ii) aliphatic amino acids (glycine, alanine, valine, leucine, isoleucine and methionine); (iii) basic ionisable amino acids (histidine, lysine and arginine); (iv) acidic ionisable amino acids (aspartic acid and glutamic acid); (v) amino acid amides (asparagine and glutamine); and (vi) hydroxylated amino acids (serine and threonine). Some authors would include cysteine in this last group.

The polynucleotides that code for the polypeptides of the invention described in the invention correspond to variants of these obtained by site-directed mutagenesis of the region coding for the RT isolated from a strain of HIV-1 group O (SEQ ID NO 2). These polynucleotides correspond to the nucleotide sequence that constitutes the coding sequence of the polypeptide of the invention, hereafter called polynucleotides of the invention.

The terms "polynucleotide", "nucleotide sequence", "sequence of nucleotides", "nucleic acid" and "oligonucleotide" are used here interchangeably and refer to a polymeric form of nucleotides of any length that may or may not be biochemically modified.

Thus a second object of the invention refers to the polynucleotide sequence that codes for the polypeptide of the invention, hereafter the polynucleotide of the invention, and that has higher activity than the WT enzyme at temperatures exceeding 68° C. maintaining copying fidelity of the original enzyme and characterised in that its sequence is at least 50% identical to the parental sequence SEQ ID NO 2 and in that the polypeptide that it codes for has the changes in its amino acid sequence described above.

Thus a preferred object of the invention is the polynucleotide that codes for the polypeptide of the invention with changes of amino acids K358R, A359G and S360A (reverse transcriptase RTO_3M). In a particular embodiment of the invention, the polynucleotide of the invention corresponds to SEQ ID NO 4.

Another preferred object of the invention is the polynucleotide that codes for the polypeptide of the invention with changes in amino acids K358R, A359G and S360A and additionally the substitutions T355A and Q357M (reverse transcriptase RTO_5M). In a particular embodiment, the polynucleotide of the invention corresponds with SEQ ID NO 6.

Thus, another preferred object of the invention is the polynucleotide that codes for the polypeptide of the invention with changes in amino acids K358R, A359G and S360A and additionally T69SSG (reverse transcriptase RTO_T69SSG_3M). In a particular embodiment, the polynucleotide of the invention corresponds with SEQ ID NO 8.

Another preferred object of the invention is the polynucleotide that codes for the polypeptide of the invention with changes in amino acids K358R, A359G and S360A and additionally the substitution E478Q (reverse transcriptase RTO_E478Q_3M). In a particular embodiment, the polynucleotide of the invention corresponds to SEQ ID NO 10.

Thus, in another preferred object of the invention, reverse transcriptases RTO_3M, RTO_5M, RTO_T69SSG_3M and RTO_E478Q_3M have nucleotide sequences that code for the MNS flanking polypeptide sequences at the N-terminal end and the histidine tail at the C-terminal end, giving rise to the polynucleotides that code for the reverse transcriptases RTO_3M*, RTO_5M*, RTO_T69SSG_3M* and RTO_E478Q_3M*, that in a particular object correspond to the nucleotide sequences SEQ ID NO 14, SEQ ID NO 16, SEQ ID NO 18 and SEQ ID NO 20 respectively.

Considering that the RTs of different circulating strains and isolates of HIV can be evolutionarily similar, it is hoped that the global identity of the genes that code them be equal to or greater than 50%, and more specifically at the level of the polynucleotide sequence corresponding to SEQ ID NO 2 (the RTO_WT) be of 60% or greater. In addition, the degree of identity or homology between the amino acid sequences of the RTs that are the object of the invention and the sequences of other similar RTs can be determined by methods known in the state of the art. For example, through the alignment of the amino acid sequence of the putative RT and that corresponding to RTO_3M of this document.

The term "homology" as used in this document refers to the similarity between two structures due to a common evolutionary ancestry and more specifically to the similarity or identity between the nucleotides of equivalent positions in two or more polynucleotides.

The term "identity" as used in this document refers to the proportion of identical nucleotides between two polynucleotides that are compared. The methods for comparing sequences are known in the state of the art and include, although without limitation, the BLASTP or BLASTN, ClustalW and FASTA programs. Given that two proteins are considered homologous if they have the same evolutionary origin or if they have similar function and structure, it is generally assumed that values of similarity or identity higher that 30% indicate homologous structures. We can therefore consider that identity percentages of at least 80% will maintain the same properties of the polypeptide.

Human immunodeficiency viruses (HIV-1 and HIV-2) are aetiological agents of AIDS in humans. They belong to the genus Lentivirus within the Retroviridae family (retrovirus), where one of their main characteristics is enormous genetic diversity. HIV-1 has been classified into four groups: M, O, N and P. The first isolate of HIV-1 group O was obtained from patients infected in 1987 and their nucleotide sequence was published three years later (De Leys et al. *J. Virol.* 1990; 64: 1207-1216). Currently, variants of HIV-1 group O (for example strain MVP5180/91) can be obtained from NIH AIDS Research & Reference Reagent Program (www.aidsreagent.org) (Germantown, Md., USA). The information contained in this invention will also enable an expert in the state of the art to generate variants of RT with higher thermostability than the original enzyme, starting from the sequence of RTs of different strains.

The term "isolated" as used in this document refers to nucleotides or peptides that: 1) are substantially free of components that normally accompany them or interact with them in nature, or 2) if they are found in natural medium, have been synthetically (not naturally) altered by human intervention and/or introduced into a cell that does not normally contain them. For example, a natural polynucleotide becomes an "isolate" if it has been altered by human intervention (by means of, for example but without limitation, site-directed mutagenesis, adding insertions and/or deletions, etc.). Similarly, a natural polynucleotide becomes an "isolate" if it is introduced by non-natural means into a non-native organism for this polynucleotide (transfection). Therefore the term "isolate" in this latter case is equivalent to the term "heterologous".

With the information provided in this invention an expert in the field would be able to identify nucleotide sequences homologous to those described in this invention that code for RTs with identical characteristics to those described for the RT of the invention. Therefore, the polynucleotide of the invention constitutes the sequence coding for a variant of RT isolated from a HIV-1 group O with the improved activity described, where the nucleotide sequence corresponds to:

a) molecules of nucleic acid of the isolated polynucleotide sequence or in its complementary chain,
b) molecules of nucleic acid where the complementary chain is able to hybridise with a polynucleotide sequence of (a), or
c) molecules of nucleic acid where the sequence differs from (a) and/or (b) due to the degeneration of the genetic code.

The polynucleotide of the invention can be isolated as such or as being a component of vectors that enable the propagation of these polynucleotides in suitable host cells. Therefore, in another object, the invention refers to a vector, hereafter called the vector of the invention that comprises the polynucleotide of the invention as previously described.

The vector can be, for example, a cloning vector or an expression vector. Preferably, this vector is a suitable plasmid for expression and purification of the RT of the invention.

The term "cloning vector" as used in this description refers to a DNA molecule in which another fragment of DNA may be integrated, without losing the capacity for self-replication. Examples of expression vectors are, but without limitation plasmids, cosmids, DNA phages or artificial yeast chromosomes.

The term "expression vector" as used in this description refers to a cloning vector suitable for expressing a nucleic acid that has been cloned in it after being introduced into a cell, called the host cell. This nucleic acid is generally operationally bound to control sequences.

The term "expression" refers to the process in which a polypeptide is synthesised starting from a polynucleotide. It includes the transcription of the polynucleotide into a messenger RNA (mRNA) and the translation of this mRNA into a protein or polypeptide.

The term "hosting cell" or "host cell" as used in this description refers to any prokaryotic or eukaryotic organism that is the recipient of the expression or cloning vector or of any other DNA molecule.

Suitable vectors for the insertion of the polynucleotide of the invention are plasmids used for the expression of proteins in prokaryotes such as, by way of illustration, pUC18, pUC19, Bluescript and derivatives, mp18, mp19, pBR322, pMB9, Co1E1, pCR1, RP4, phages and "shuttle" vectors such as pSA3 and pAT28; expression vectors in yeasts such as the 2 micron plasmid of *Saccharomyces cerevisiae*, integration plasmids, YEP vectors, centromere plasmids and similar; expression vectors in insect cells such as the vectors of the pAC and pVL series of expression vectors; expression vectors in plants such as piBi, pEarleyGate, PAVA, pCAMBIA, PGSA, PGWB, PMDC, PMY, spores and similar, and other expression plasmids of proteins used in eukaryotic cells, including baculovirus suitable for transfection of insect cells using any system available in the state of the art.

As used in this document, a "host cell" or "hosting cell" includes any cultivable cell that can be modified by the introduction of DNA that is not naturally contained in the cell, hereafter called the host cell of the invention.

Preferably, a host cell is one in which the polynucleotide of the invention can be expressed, giving rise to a stable polypeptide, post-translationally modified and located in a suitable subcellular compartment. The choice of a suitable host cell may also be influenced by the choice of detection signal. For example, the use of constructions with reporter genes (for example, lacZ, luciferase, thymidine kinase or green fluorescent protein "GFP") can provide a selectable signal through the activation or inhibition of transcription of the gene of interest in response to a protein regulating transcription. In order to achieve optimum selection or "screening", the phenotype of the host cell should be considered.

A host cell of the invention includes prokaryotic and eukaryotic cells. The prokaryotes may include gram negative (for example *Escherichia coli*) or gram positive (for example bacteria of the *Bacillus* genus) organisms. Prokaryotic cells will be preferably used for the propagation of the transcription control sequence of the vector which contains the polynucleotide(s) of the invention, which enables obtaining a higher number of copies of the vector containing the polynucleotide(s) of the invention. Suitable prokaryotic host cells for the transformation of this vector include, for example but without limitation *E. coli, Bacillus subtilis, Salmonella typhimurium*, and other species of the genera *Pseudomonas, Streptomyces* and *Staphylococcus*. Eukaryotic host cells include yeast cells, plant cells, fungal cells, insect cells, mammalian cells and cells of parasitic organisms (for example *Trypanosomes*). As used in this document, the term yeast includes not only yeast in the strict taxonomic sense, that is unicellular organisms, but also multicellular fungi similar to yeast and filamentous fungi. Examples of species are *Kluyveromyces lactis, Schizosaccharomyces pombe*, and *Ustilago maydis*, with *Saccharomyces cerevisiae* and *Pichia pastoris* as preferred organisms. Other yeasts that can be used in the production of the poly-amino-acid sequences of the invention are *Neurospora crassa, Aspergillus niger, Aspergillus nidulans, Candida tropicalis*, and *Hansenula polymorpha*. The culture systems with mammalian host cells include established cell lines such as COS cells, L cells, 3T3 cells, Chinese hamster ovary cells (CHO), embryonic stem cells, with BKH, HeK or HeLa as the preferred cells. Eukaryotic cells are preferably used for expression of the recombinant gene by applying the transcription regulation sequence or expression vector of the invention.

Thus another object of the invention refers to a method for obtaining the polypeptide of the invention that comprises:

1) Introducing the vector of the invention into a suitable host cell (host cell of the invention),
2) Cultivating the host cell of the invention in a suitable medium, and,
3) Purifying the polypeptide of the invention with RT activity.

A culture of host cells refers to the process of maintaining and growing the host cells. Cell cultures require controlled conditions of temperature, pH, gas percentages (oxygen and carbon dioxide) as well as the presence of suitable nutrients to enable viability and cellular division. Cell cultures can be performed in solid substrates such as agar or in liquid medium, which enables the culture of large amounts of cells in suspension.

The term "purify" as used in this description refers to the isolation of the polypeptide of the invention and to its concentration from the other polypeptides present in the culture medium of the host cell of the invention. Isolation of the RT can be carried out by means of differential solubility techniques, chromatography, electrophoresis or isoelectric focusing. Chromatographic techniques can be based on the molecular weight, ionic charge (based on the ionisation state of the amino acids in working conditions), affinity of the protein for certain chromatographic matrices or columns or by purification tags and can be performed in columns, on paper or plates. Isolation of the protein can be performed, for example, by precipitation with ammonium sulphate, fast protein liquid chromatography (FPLC) or high performance liquid chromatography (HPLC), using automated systems that notably reduce purification time and increase purification yield.

The expression "purification tag" or "affinity tag" as used in this description refers to an amino acid sequence that has been incorporated (generally by genetic engineering) into a protein to facilitate purification. The tag, which can be another protein or short sequence of amino acids, enables the purification of the protein, for example by affinity chromatography. Purification tags known in the state of the art are, for example but without limitation, calmodulin binding peptide (CBP), the enzyme glutathione S-transferase (GST) or a tail of histidine residues.

Another object of the invention refers to the method for obtaining the polynucleotide of the invention, hereafter the method of the invention, that could be performed, for example but without limitation, by site-directed or random mutagenesis starting from a non-mutated polynucleotide, chemical synthesis of the complete polynucleotide or by assembly of DNA fragments that code for different portions of the sequence to be obtained.

Another object of the invention refers to the use of the polynucleotide of the invention for obtaining the polypeptide of the invention with RT activity.

Another object of the invention refers to the use of the host cell of the invention to obtain the polypeptide of the invention. Preferably, the host cell of the invention is a bacterium, more preferably *Escherichia coli*.

The RTs stable at elevated temperatures such as the polypeptide of the invention, are useful in applications such as amplification of difficult RNAs, that is those containing secondary structures and/or sequences rich in G:C base pairs.

Thus another object of the invention is the use of the polypeptide of the invention in any of the applications or methods already known in the state of the art.

A particular object of the invention refers to a method of reverse transcription of a nucleic acid template, preferably mRNA or miRNA, that comprises:
  a) mixing the template nucleic acid with the RT of the invention, and
  b) incubating the mixture of step (a) in conditions that enable the synthesis of DNA that is complementary to the template nucleic acid.

Another particular object of the invention refers to a method of amplification of a nucleic acid template, preferably mRNA or miRNA that comprises:
  a) mixing the nucleic acid with the RT of the invention and with a DNA-dependent polymerase, and
  b) incubating the mixture of step (a) in conditions that enable the amplification of the DNA complementary to the template nucleic acid.

Another particular object of this invention refers to a method of sequencing a nucleic acid, preferably mRNA or miRNA that comprises:
  a) putting the nucleic acid in contact with the RT of the invention,
  b) incubating this mixture in conditions that enable the synthesis of a population of DNA molecules that are complementary to the template nucleic acid, and
  c) separating this population of molecules of complementary DNA to determine the nucleotide sequence.

The term "reverse transcription" or "retrotranscription" as used in this description refers to the synthesis of a DNA that is complementary to a RNA.

The term "amplification" as used in this description refers to the increase in the number of copies of a template nucleic acid. In a preferred embodiment, amplification takes place by PCR.

The term "sequencing" as used in this description refers to the determination of the order of the nucleotides of a template nucleic acid.

The term "template nucleic acid" or "template" as used in this description refers to a single or double chain nucleic acid molecule that is to be reverse transcribed, amplified or sequenced.

The expression "conditions that enable the synthesis of complementary DNA" refers to the conditions in which nucleotides can be added to a nascent DNA by base complementarity with the template nucleic acid.

The conditions in which DNA synthesis takes place generally include: (a) putting the template nucleic acid in contact with the RT of the invention in a mixture that also comprises a primer, bivalent cation, for example $Mg^{2+}$, and nucleotides, and (b) subjecting this mixture to a sufficient temperature so that a DNA polymerase, for example the RT of the invention, initiates the incorporation of nucleotides to the primer by base complementarity with the template nucleic acid, giving rise to a population of complementary DNA molecules of different sizes. The separation of this population of complementary DNA molecules enables determining the nucleotide sequence of the template nucleic acid.

The incorporation of badly paired nucleotides during complementary DNA synthesis can result in one or more mismatched bases. Therefore the synthesised DNA chain may not be exactly complementary to the template nucleic acid.

The expression "conditions that enable the synthesis of a population of complementary DNA molecules to the template nucleic acid" refers to the conditions in which sequencing is performed and that generally include (a) putting the template nucleic acid in contact with the RT of the invention in a mixture that also comprises a primer, bivalent cation, for example $Mg^{2+}$, and nucleotides, generally dNTPs and at least one ddNTP and (b) subjecting this mixture to a sufficient temperature so that a DNA polymerase, for example the RT of the invention, initiates the incorporation of nucleotides to the primer by base complementarity with the template nucleic acid, giving rise to a population of complementary DNA molecules of different sizes. The separation of this population of complementary DNA molecules, generally by electrophoresis, enables determining the nucleotide sequence of the template nucleic acid.

The term "primer" as used here refers to an oligonucleotide able to act as a starting point for DNA synthesis when it hybridises with the template nucleic acid. Preferably, the primer is an oligonucleotide of deoxyribose.

Primers can be prepared by any suitable method including, for example but without limitation, cloning and restriction of suitable sequences and direct chemical synthesis. Primers can be designed to hybridise with specific nucleic acid sequences in the template nucleic acid (specific primers) or can be synthesised at random (arbitrary primers).

The term "specific primer" as used in this description refers to a primer where the sequence is complementary to a specific nucleotide sequence in the template nucleic acid to be reverse transcribed, amplified or sequenced.

The term "arbitrary primer" refers to a primer where the sequence is synthesised at random and that is used to initiate the synthesis of DNA in random positions of the template nucleic acid to be reverse transcribed, amplified or sequenced. A population of different arbitrary primers is frequently used. The term "arbitrary primers" refers to a set of primers where the sequence is synthesised at random and that is used to initiate DNA synthesis in random positions of the template nucleic acid to be reverse transcribed, amplified or sequenced.

The term "hybridisation" as used in this description refers to the pairing of two molecules of complementary single-stranded nucleic acid (DNA and/or RNA) molecules to result in a double-stranded molecule. Preferably, complementarity is 100%. That is, in the region of complementarity, each nucleotide of one of the two nucleic acid molecules can form hydrogen bonds with a nucleotide present in the other nucleic acid molecule. However, those with normal experience in the field will recognise that two molecules of nucleic acid that have a region of complementarity of less than 100% can also hybridise.

The term "nucleotide" as used in this description refers to an organic molecule formed by the covalent binding of a pentose, nitrogenous base and a phosphate group. The term nucleotide includes deoxyribonucleoside triphosphates (dNTPs) such as, for example but without limitation, dATP, dCTP, dITP, dUTP, dGTP, dTTP or their derivatives. The term nucleotide also includes dideoxyribonucleoside triphosphates (ddNTPs) such as, for example, ddATP, ddCTP, ddGTP, ddITP, ddTTP or their derivatives. In accordance with this invention, a "nucleotide" or a "primer" can be marked or labelled by well-known techniques in the state of the art. Detectable labels include, for example, radioactive isotopes, fluorescent labels, chemiluminescent labels, bioluminescent labels or enzymatic labels.

The term "DNA-dependent DNA polymerase" as used in this description refers to a DNA polymerase capable of catalysing the polymerisation of deoxyribonucleotides using DNA as the template nucleic acid. Examples of DNA-dependent DNA polymerases that can be used in the method of amplification of this invention are, without limitation, DNA polymerases of *Thermus thermophilus* (Tth), *Thermus aquaticus* (Taq), *Thermotoga neapolitana* (Tne), *Thermotoga maritima* (Tma), *Thermococcus litera/ls* (Tli o Vent™), *Pyrococcus furiosus* (Pfu), *Pyrococcus* sp. GB-D (Deep Vent™) *Pyrococcus waasii* (Pwo), *Bacillus stearothermophilus* (Bst), *Bacillus caldaphilus* (Bca), *Sulfolobus acidocaldarius* (Sac), *Thermoplasma acidophilum* (Tac), *Thermus flavus* (Tfl/Tub), *Thermus ruber* (Tru), *Thermus brockianus* (DyNAzyme™), *Methanobacterium thermoautotrophicum* (Mth) or *Mycobacterium* sp. (Mtb, Mlep).

Another object of the invention refers to a kit comprising the necessary components for carrying out any of the methods previously described in this description, hereafter the kit of the invention.

A preferred embodiment of this object of the invention refers to a kit of the invention to perform any of the methods previously described in the description and that comprises:
a) the RT of the invention, and
b) at least one component of the list comprising:
 i) a buffer
 ii) a primer
 iii) a DNA-dependent DNA polymerase
 iv) a nucleotide.

A particular object of the invention refers to the use of the kit of the invention for reverse transcription, amplification or sequencing of a template nucleic acid where this is preferably messenger RNA (mRNA) or a microRNA (miRNA) or a miRNA precursor.

Throughout the description and the claims, the word "comprise" and its variants does not exclude other technical characteristics, additives, components or steps. For experts in the field, other objects, advantages and characteristics of the invention will emerge, partly from the description and partly from the practice of the invention. The following examples and figures are provided for illustration of the invention and are not intended to be limiting of this invention.

EXAMPLES

Figure 1A:
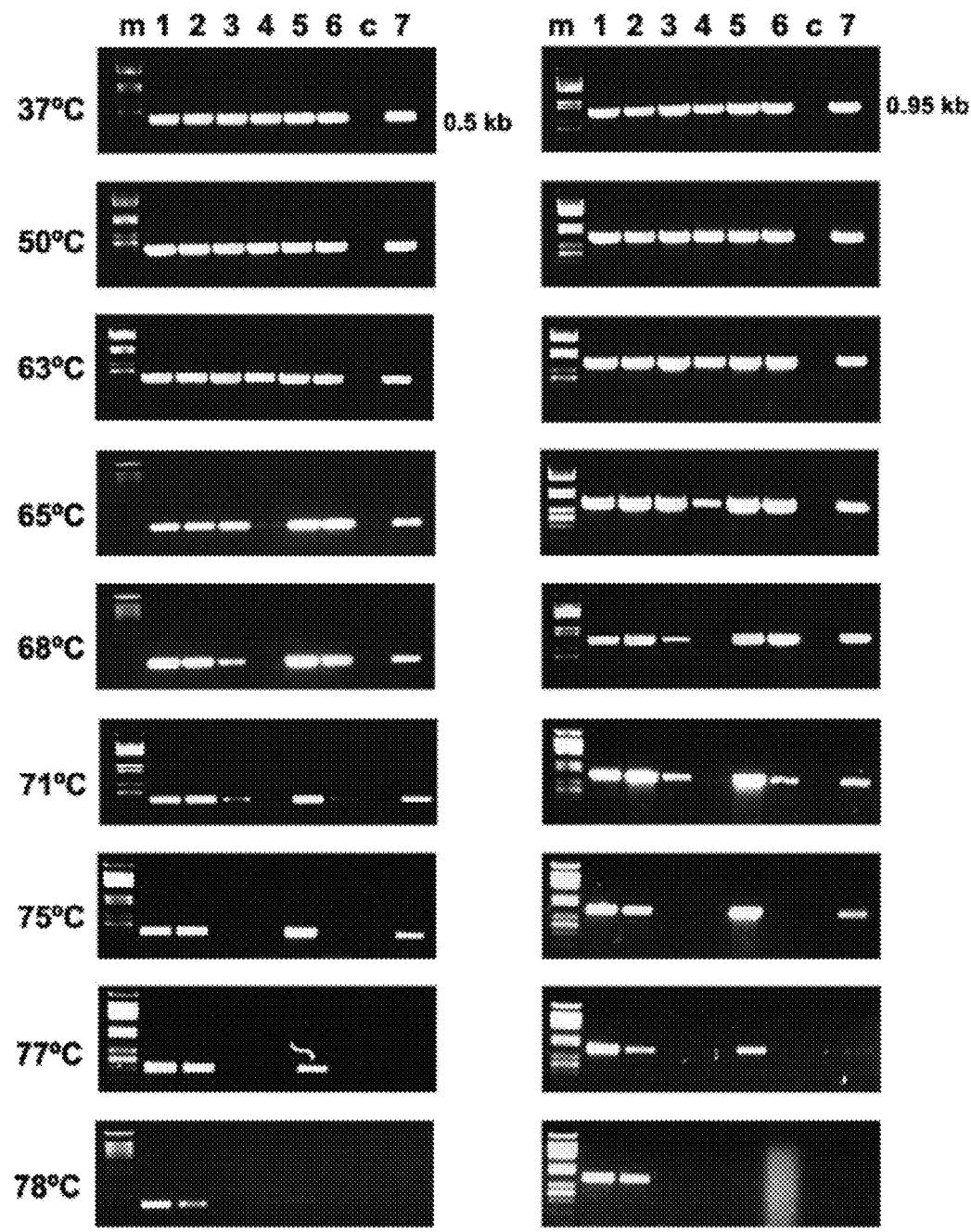
FIG. 1. Amplification by RT-PCR of RNA fragments coding for actin (approximately 500 and 950 base pairs) from total RNA of mouse liver. Amplification was performed with the enzymes indicated: (A) RT of HIV-1 group O "wild-type" (RTO_WT*) (well 7), and mutants K358R/A359G/S360A (RTO_3M*) (well 1), T355A/Q357M/K358R/A359G/S360A (RTO_5M*) (well 2), K65R/K358R/A359G/S360A (well 3), K65R/V75I/K358R/A359G/S360A (well 4), K358R/A359G/S360A/E478Q (RTO_E478Q_3M*) (well 5) and K65R/K358R/A359G/S360A/E478Q (well 6). (B) Mutants of the HIV-1 group O RT: K358R/A359G/S360A (RTO_3M*) (well 1), T69SSG/K358R/A359G/S360A (RTO_T69SSG_3M*) (well 2), V148I/K358R/A359G/S360A (well 3) and F61A/K358R/A359G/S360A (well 4). The temperatures indicated refer to the DNA copy synthesis reaction. Wells m and c show low molecular weight markers (DNA of phi29 phage digested with HindIII) and a negative control (without cDNA) respectively. All mutations indicated were introduced in the context of the RTO_WT sequence.
Figure 1B:
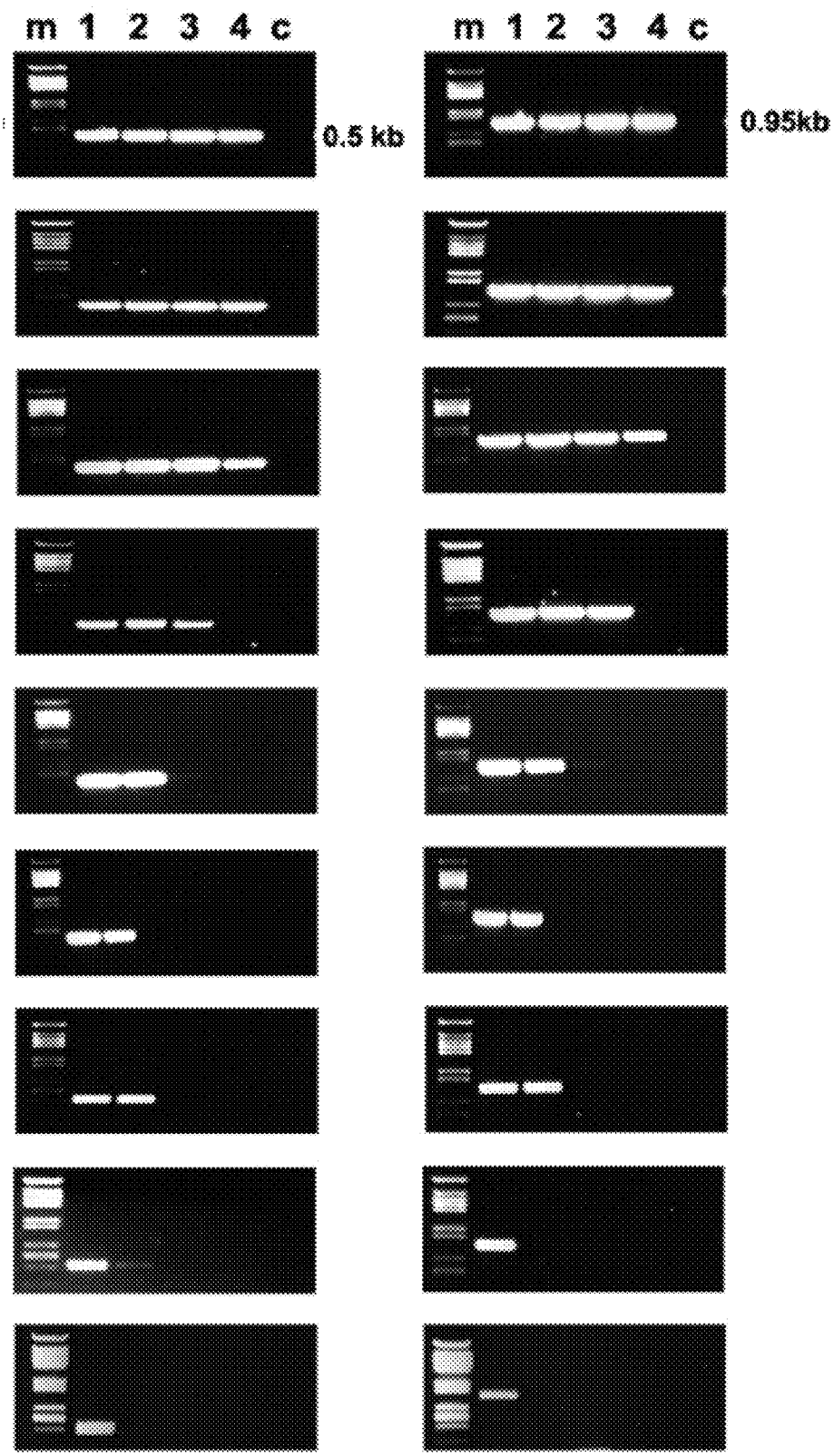

Effect of Reverse Transcription Reaction Temperature on the Effectiveness of the RT-PCR Reaction Using Different Mutants of RT of HIV-1 Group O The efficiency of the reverse transcription reaction at different temperatures was determined after amplification by PCR of the DNA copy obtained. The mutants K358R/A359G/S360A (RTO_3M*), K358R/A359G/S360A/E478Q (RTO_E478Q_3M*), T355A/Q357M/K358R/A359G/S360A (RTO_5M*) and T69SSG/K358R/A359G/S360A (RTO_T69SSG_3M*) were more effective than "wild-type RT of HIV-1 group O (RTO_WT*) and other mutant RTs in the amplification of RNA fragments of approximately 500 and 950 base pairs derived from the actin gene, in reverse transcription reactions carried out at different temperatures in the range of 37 to 78° C. (FIG. 1).

Figure 2:
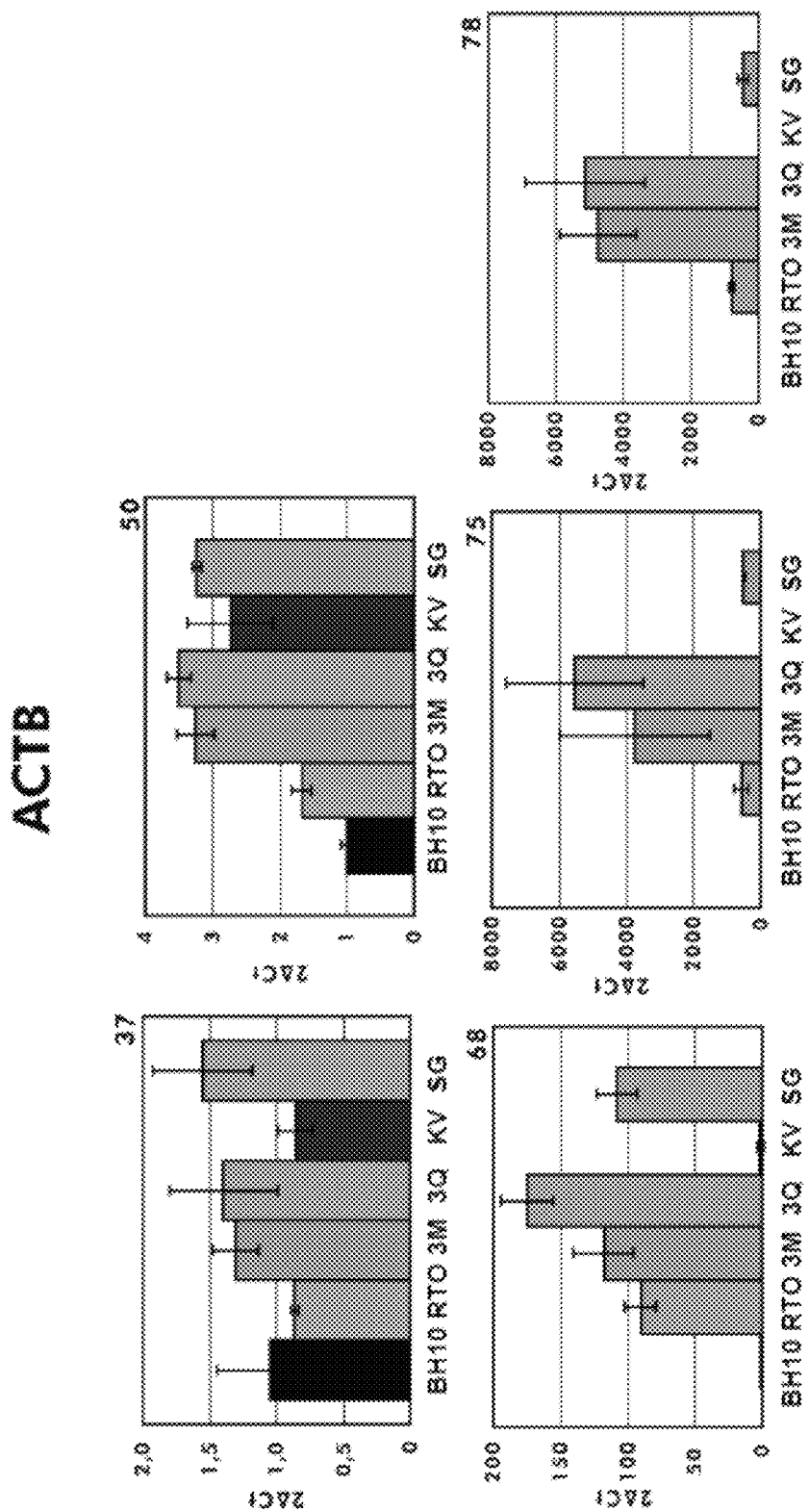
FIG. 2. Shows the reverse transcription efficiency estimated by real time PCR for the wild-type RTs isolated from HIV-1 group M subtype B BH10 (BH10) and group O (RTO_WT*; indicated as RTO in the figure) together with the mutants that are objects of this patent RTO_3M* (3M), RTO_E478Q_3M* (3Q) and RTO_T69SSG_3M* (SG) and a reference mutant bearing the changes characteristic of 3M, together with K65R and V75I (K65R/V75I/K358R/A359G/S360A, KV). (ACTB) represents amplifications of messenger RNA of actin and (GAPDH) of messenger RNA of glyceraldehyde 3-phosphate dehydrogenase. The temperature at which the reverse transcription reaction was performed is shown at the top right of each histogram.
Figure 2:
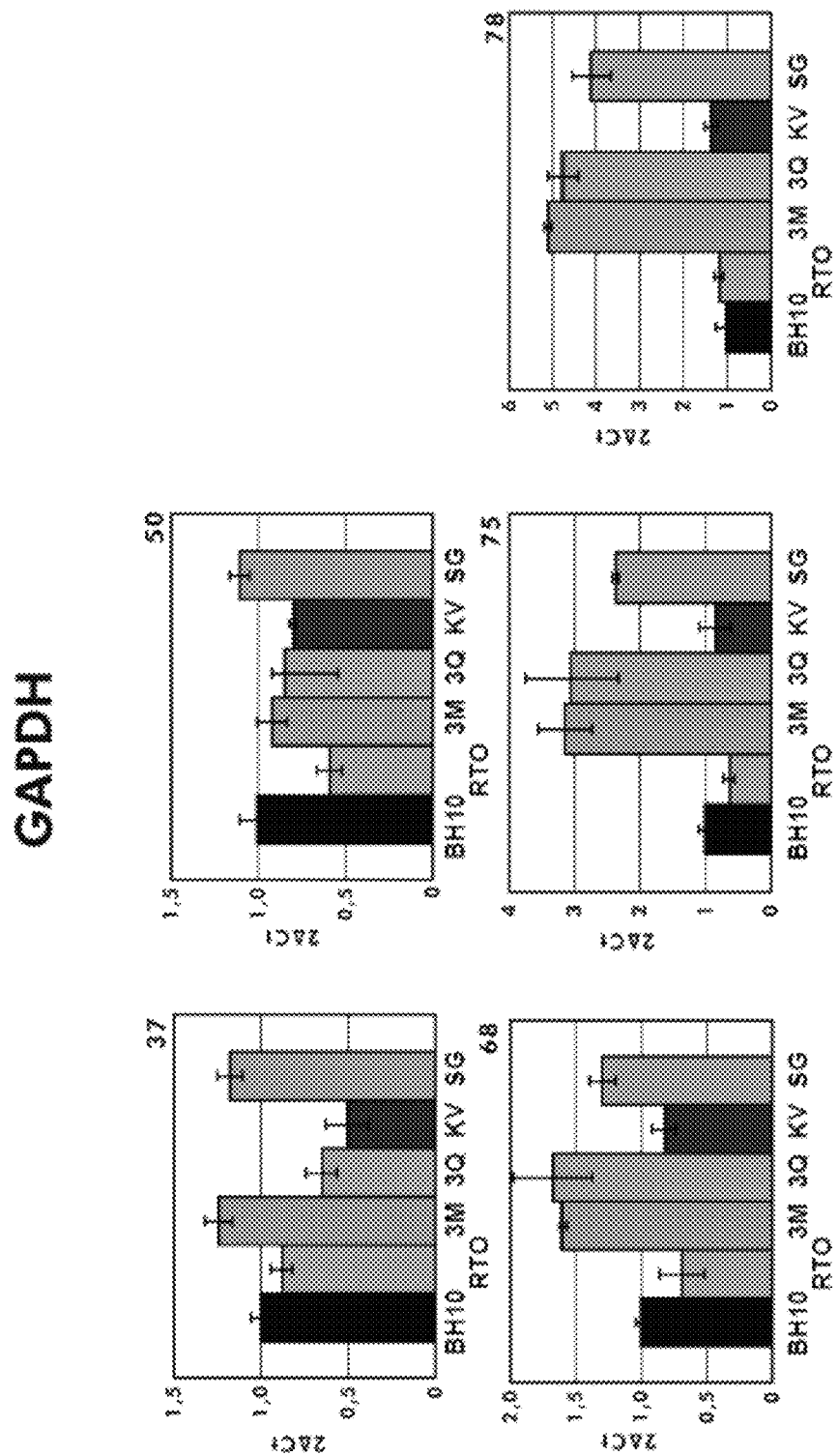

These results were consistent with those obtained in the amplification of sequences derived from messenger RNAs of actin or of glyceraldehyde-3-phosphate dehydrogenase (GAPDH) in real time PCR reactions. In both cases, the effectiveness of reverse transcription of mutants RTO_3M* and RTO_E478Q_3M* was observed to be significantly higher than that of the "wild-type" RT at temperatures of 75 and 78° C. (FIG. 2). In the case of mutant RTO_T69SSG_3M*, the effectiveness of amplification was observed to be higher than that of the "wild-type" enzyme for the RNA of GAPDH and similar for the RNA of actin.

Figure 3:
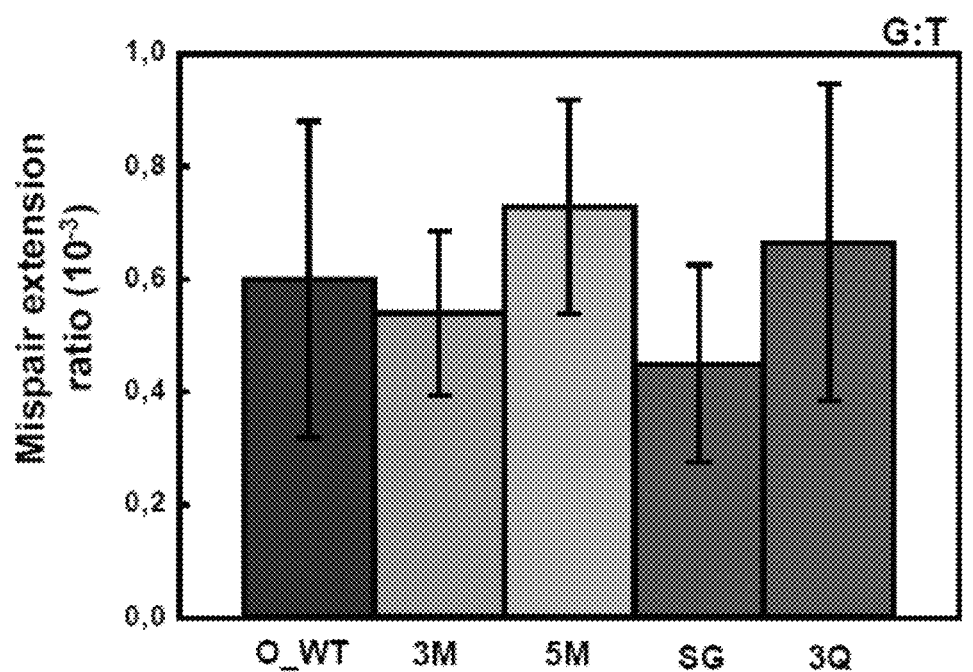
FIG. 3. Shows the efficiency of extension of mispaired ends (G:T, G:G and G:A) of the mutant RTs RTO_3M* (3M), RTO_5M* (5M), RTO_T69SSG_3M* (SG) and RTO_E478Q_3M* (3Q) in comparison with RTO_WT* (O_WT).
Figure 3:
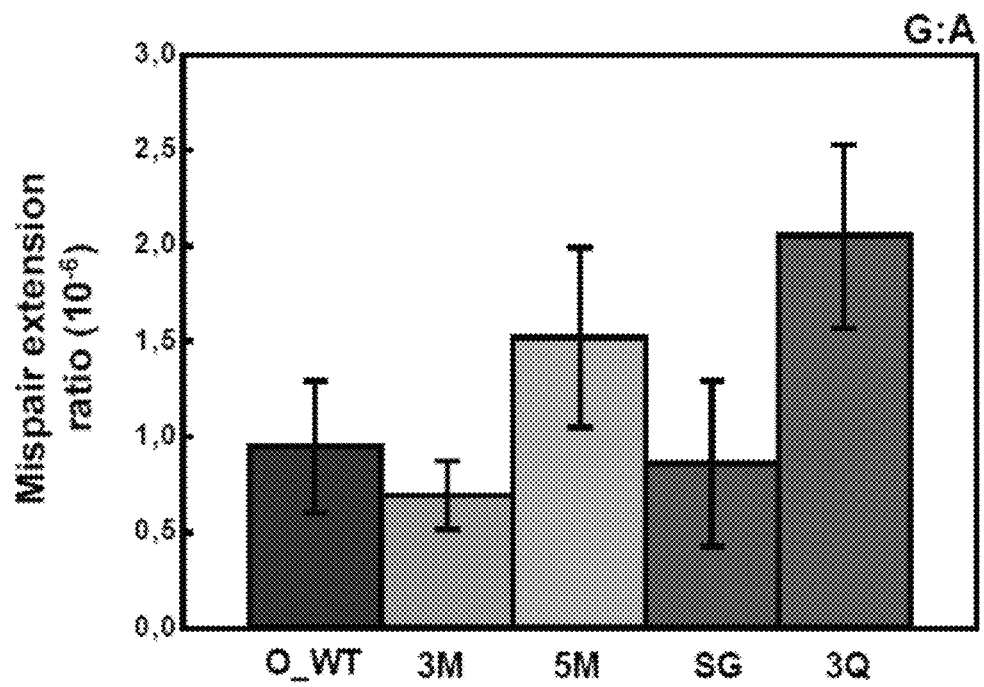
Figure 3:
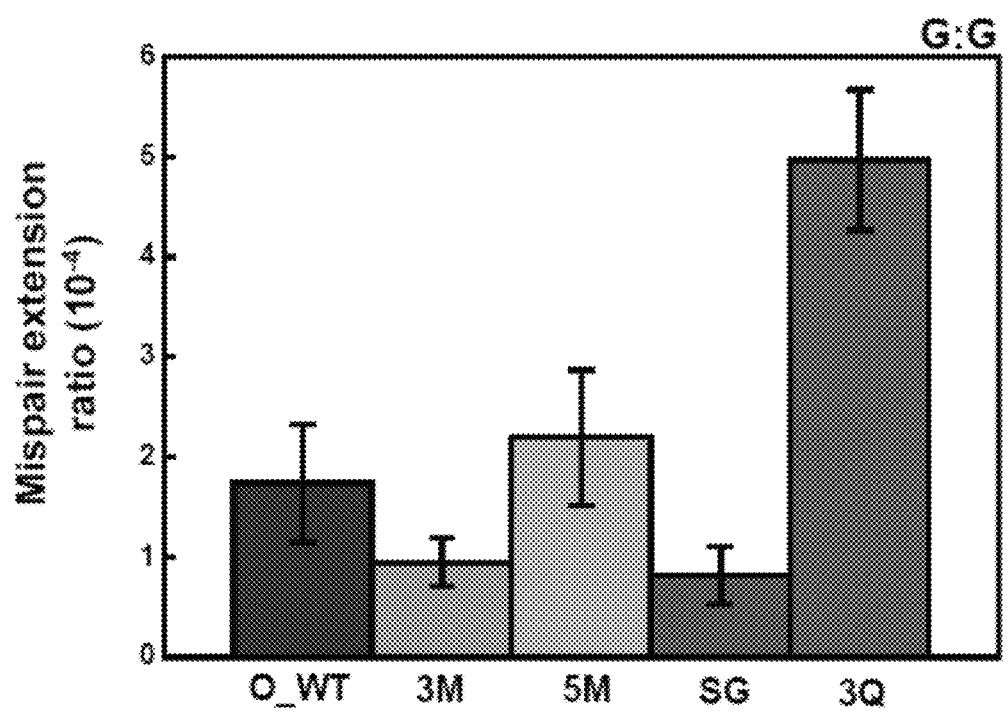

Copying Fidelity of the Mutants with the Highest Activity at Elevated Temperatures Reverse transcriptases RTO_3M*, RTO_5M* and RTO_E478Q_3M* showed similar catalytic activity to that of the "wild-type" enzyme (RTO_WT*) in assays of incorporation of a single nucleotide (Table 2), although the catalytic effectiveness ($k_{pol}/K_d$) of mutant RTO_T69SSG_3M* was slightly less than that of the wild type enzyme. No significant differences were found between the enzymes studied in extension assays of the 3' mispaired G:T end. In the extension of the G:A and G:G ends, all the RTs showed similar effectiveness to that of the "wild-type" enzyme, although mutant RTO_T69SSG_3M* was more prone that the others to extend G:G or G:A ends (FIG. 3).

TABLE 2

Kinetic parameters of the extension of mispaired ends on the template-primer complex 31T/21P for the RT of "wild-type" HIV-1 group O (RTO_WT*) and mutants RTO_3M*, RTO_5M*, RTO_T69SSG_3M* and RTO_E478Q_3M*, determined in the pre-stationary state. The numbers indicated between brackets in the last column show the increase in fidelity compared to RTO_WT* of the coefficients between the extension efficiencies of the mispaired ends.

| Enzyme | Base pair at the 3' end | $k_{pol}$ (s$^{-1}$) | $K_d$ (μM) | $k_{pol}/K_d$ (μM$^{-1}$ s$^{-1}$) | Efficiency of extension of the mispaired ends ($f_{ext}$) |
|---|---|---|---|---|---|
| RTO_WT* | G:C | 32.3 ± 1.5 | 11.4 ± 1.7 | 2.83 ± 0.43 | |
| | G:T | 13.8 ± 2.8 | 8148 ± 3206 | (1.70 ± 0.75) × 10$^{-3}$ | (6.00 ± 2.80) × 10$^{-4}$ |
| | G:G | 0.56 ± 0.07 | 1132 ± 316 | (4.94 ± 1.51) × 10$^{-4}$ | (1.74 ± 0.59) × 10$^{-4}$ |
| | G:A | 0.021 ± 0.003 | 7817 ± 2334 | (2.71 ± 0.89) × 10$^{-6}$ | (9.57 ± 3.46) × 10$^{-7}$ |
| RTO_3M* | G:C | 16.4 ± 0.6 | 5.0 ± 0.7 | 3.28 ± 0.50 | |
| | G:T | 13.5 ± 1.3 | 7615 ± 1519 | (1.77 ± 0.39) × 10$^{-3}$ | (5.40 ± 1.45) × 10$^{-4}$ (1.1) |
| | G:G | 0.41 ± 0.04 | 1325 ± 249 | (3.09 ± 0.64) × 10$^{-4}$ | (9.42 ± 2.42) × 10$^{-5}$ (1.8) |
| | G:A | 0.013 ± 0.001 | 5516 ± 1061 | (2.28 ± 0.47) × 10$^{-6}$ | (6.95 ± 1.78) × 10$^{-7}$ (1.4) |
| RTO_5M* | G:C | 23.5 ± 1.4 | 9.1 ± 1.9 | 2.57 ± 0.55 | |
| | G:T | 6.08 ± 0.38 | 3249 ± 445 | (1.87 ± 0.28) × 10$^{-3}$ | (7.28 ± 1.90) × 10$^{-4}$ (0.8) |
| | G:G | 0.57 ± 0.05 | 1003 ± 211 | (5.65 ± 1.27) × 10$^{-4}$ | (2.19 ± 0.68) × 10$^{-4}$ (0.8) |
| | G:A | 0.029 ± 0.003 | 7512 ± 1552 | (3.91 ± 0.89) × 10$^{-6}$ | (1.52 ± 0.47) × 10$^{-6}$ (0.6) |
| RTO_E478Q_3M* | G:C | 27.7 ±1.0 | 12.5 ± 1.6 | 2.21 ± 0.30 | |
| | G:T | 11.1 ± 2.0 | 7566 ± 2725 | (1.47 ± 0.59) × 10$^{-3}$ | (6.65 ± 2.81) × 10$^{-4}$ (0.9) |
| | G:G | 0.54 ± 0.01 | 489 ± 16 | (1.10 ± 0.04) × 10$^{-3}$ | (4.97 ± 0.70) × 10$^{-4}$ (0.4) |
| | G:A | 0.029 ± 0.002 | 6362 ± 1110 | (4.54 ± 0.86) × 10$^{-6}$ | (2.05 ± 0.48) × 10$^{-6}$ (0.5) |
| RTO_T69SSG_3M* | G:C | 21.1 ± 1.8 | 14.0 ± 4.4 | 1.51 ± 0.49 | |
| | G:T | 3.15 ± 0.36 | 4632 ± 1070 | (6.80 ± 1.75) × 10$^{-4}$ | (4.50 ± 1.86) × 10$^{-4}$ (1.3) |
| | G:G | 0.26 ± 0.01 | 2080 ± 250 | (1.23 ± 0.16) × 10$^{-4}$ | (8.14 ± 2.85) × 10$^{-5}$ (2.1) |
| | G:A | (7.6 ± 1.6) × 10$^{-3}$ | 5854 ± 1877 | (1.30 ± 0.50) × 10$^{-6}$ | (8.61 ± 4.33) × 10$^{-7}$ (1.1) |

Copying fidelity was also measured of some of these enzymes in complementation assays that use derivatives of the M13mp2 phage bearing the lacZ gene. The frequency of obtaining mutants when the synthesis process was carried out with different recombinant RTs was determined. Significant differences between copying fidelity of the mutants and the "wild-type" enzyme were also not observed in these assays (Table 3). Taken together, these data indicate that the increase in reverse transcription efficiency at high temperatures shown by the mutants described here, did not have a negative effect on the copying fidelity of the enzyme.

TABLE 3

Copying fidelity of mutants RTO_3M*, RTO_T69SSG_3M* and RTO_E478Q_3M* compared to that of RTO_WT* and estimated by genetic complementation assays (M13mp2 lacZa "forward mutation assay"). The data for RTO_WT*, obtained from two independent experiments, were published previously (Álvarez et al. *Nucleic Acids Res* 2013; 41: 4601-4612).

| RT | Total plaques | Mutant plaques | Mutant frequency | Increase in fidelity compared to RTO_WT |
|---|---|---|---|---|
| RTO_WT* | | | | |
| (experiment 1) | 7579 | 63 | 0.00831 | — |
| (experiment 2) | 3957 | 38 | 0.00960 | |
| RTO_3M* | 8394 | 74 | 0.00881 | 1.0 |

TABLE 3-continued

Copying fidelity of mutants RTO_3M*, RTO_
T69SSG_3M* and RTO_E478Q_3M* compared to that of
RTO_WT* and estimated by genetic complementation assays (M13mp2
lacZα "forward mutation assay"). The data for RTO_WT*,
obtained from two independent experiments, were published previously (Á
lvarez et al. *Nucleic Acids Res* 2013; 41: 4601-4612).

| RT | Total plaques | Mutant plaques | Mutant frequency | Increase in fidelity compared to RTO_WT |
|---|---|---|---|---|
| RTO_T69SSG_3M* | 14262 | 79 | 0.00554 | 1.6 |
| RTO_E478Q_3M* | 7802 | 52 | 0.00666 | 1.3 |

Materials and Methods

Expression and Purification of RT of Group O and of its Mutants

The expression and purification of the RTs was performed with a modified version of the p66RTB plasmid (Boretto et al. *Anal. Biochem.* 2001; 292: 139-147; Matamoros et al. *J. Mol. Biol.* 2005; 349: 451-463), that contained the ampicillin resistance gene and in which the region coding for the p66 subunit of the RT of an isolate of HIV-1 group O was cloned (Menéndez-Arias et al. *J. Biol. Chem.* 2001; 276: 27470-27479; Álvarez et al. *J Mol Biol* 2009; 392: 872-884; patent WO2010130864). RT Purification was carried out by following the procedure described by Boretto et al. (*Anal. Biochem.* 2001; 292: 139-147), which includes a step of bacterial lysis and homogenisation, followed by ion exchange chromatography (in phosphocellulose) and affinity chromatography (in $Ni^{2+}$-nitriloacetic agarose columns).

Construction of Plasmids Carrying Mutations in the Context of the RT of HIV-1 Group O The plasmids for the expression of the mutant RTs RTO_3M*, RTO_E478Q_3M*, RTO_5M* and RTO_T69SSG_3M* were obtained by site-directed mutagenesis using the "Quik-Change Site-Directed Mutagenesis" kit from Stratagene following the manufacturer's instructions.

The following mutagenic oligonucleotides were used:

```
a) to introduce the mutations K358R/A359G/S360A:
5'-GGGAAATATACTAGGCAAAGGGGCGCCCACACAAATGAC-3'

5'-GTCATTTGTGTGGGCGCCCCTTTGCCTAGTATATTTCCC-3' b) for T355A:
5'-ACAGGGAAATATGCTAGGATGAGGGGCGCC-3'
and

5'-GGCGCCCCTCATCCTAGCATATTTCCCTGT-3' c) for Q357M:
5'-GGGAAATATACTAGGATGAGGGGCGCCCACACAAATGAC-3'
and

5'-GTCATTTGTGTGGGCGCCCCTCATCCTAGTATATTTCCC-3' d) for E478Q:
5'-CCAATCAAAAGGCTCAATTAATGGCAG-3'
and

5'-CTGCCATTAATTGAGCCTTTTGATTGG-3' e) to introduce the change T69S, with the
insertion Ser-Gly:
5'-GCTATAAAAAGAAAGATAGTAGTTCCGGGAAGTGGAGAAAGCT
GGTAGAC-3'
```

```
-continued
5'-GTCTACCAGCTTTCTCCACTTCCCGGAACTACTATCTTTCTTTTT
TATAGC-3'
```

The plasmid carrier of the sequence coding for p66 of "wild-type" HIV-1 group O was used as template for the introduction of K358R/A359G/S360A as previously described (Álvarez et al. *J Mol Biol* 2009; 392: 872-884; patent WO2010130864). Mutations T355A and E478Q and mutation T69S (associated with the insertion SG) were separately introduced into the plasmid carrier of K358R/A359G/S360A to obtain the mutants: T355A/K358R/A359G/S360A, K358R/A359G/S360A/E478Q and T69SSG/K358R/A359G/S360A. Finally the change Q357M was introduced in the expression plasmid carrier of the change T355A/K358R/A359G/S360A in order to obtain the mutant T355A/Q357M/K358R/A359G/S360A. In all cases, after mutagenesis, it was checked that the sequence of the region coding for p66 in these plasmids was correct and contained only the mutations introduced.

Effect of Mutations on the Efficiency of the Coupled Reverse Transcription Reaction with Amplification by PCR Reverse transcription reactions were carried out at different temperatures and then the reaction products (cDNA) were amplified by PCR in standard conditions (Álvarez et al. *J Mol Biol* 2009; 392: 872-884). Typically, the reverse transcription reaction was carried out in a volume of 20 μl (4 μl of 250 mM Tris-HCl buffer (pH 8.3 at 25° C.) containing 375 mM KCl, 15 mM $MgCl_2$ and 50 mM dithiothreitol; 1 μl of total RNA isolated from mouse liver (1 μg/μl); 4 μl of a mixture of the 4 dNTPs (at 2.5 mM each); 1 μl of oligo$(dT)_{16}$ (100 μM); 0.5 μl of ribonuclease inhibitor (40 units/μl); RT at an approximate concentration of 150 nM and the rest up to 20 μl of water). Initially, the RNA and the oligo dT were incubated at 68° C. for 3 min. Then the other reaction components were added (including the RT) and incubated for 1 hour at the desired temperature to obtain the cDNA. Finally the reaction was stopped by incubating for 10 min at 92° C. to inactivate the enzyme. The cDNA was amplified by PCR in standard conditions using Taq polymerase or other similar enzymes (for example, Expand High Fidelity DNA polymerase).

Real Time PCR

The efficiency of reverse transcription of RTs was determined at various temperatures (37, 50, 68, 75 and 78° C.) by real time PCR. To do this, three independent reactions were performed in each experiment. All the reactions were carried out in a volume of 20 μl in 50 mM Tris-HCl buffer (pH 8.3) containing 75 mM KCl, 3 mM $MgCl_2$, 10 mM dithiothreitol, 1 U/μl of ribonuclease inhibitor (RNasin® Plus, Promega), 500 μM of each dNTP, 5 μM of oligo$(dT)_{16}$, 50 ng/μl of total RNA of mouse liver (Stratagene) and the corresponding RT at 150 nM. Hybridisation of the template RNA with the oligo$(dT)_{16}$ and the cDNA synthesis reaction were carried out in the conditions described in the previous section.

Efficiency of reverse transcription was determined by quantitative PCR (qPCR), calculating the relative amount of cDNA produced from the messenger RNAs of β-actin and glyceraldehyde 3-phosphate dehydrogenase (GAPDH). To do this, the oligonucleotides 5'-CTAAGGCCAACCGT-GAAAAG-3' and 5'-ACCAGAGGCATACAGGGACA-3' were used for actin, and 5'-CTCCCACTCTTCCACCT-TCG-3' and 5'-CATACCAGGAAATGAGCTTGACAA-3' for GAPDH. The amplification by PCR reactions were made in triplicate in a final volume of 10 μl with an amount of cDNA approximately equal to 5 ng of total RNA, 250 nM of each oligonucleotide ("primer") and 5 μl of Power Sybr Green PCR Master Mix (Applied Biosystems PN 4367659), that included AmpliTaq Gold® DNA polymerase, dNTPs and the other reagents necessary to carry out the PCR reaction. MicroAmp® Optical 384-well Reaction Plates with bar codes were used (Applied Biosystems PN 4309849). After an initial denaturation stage at 95° C. (10 min), the samples were subjected to 40 amplification cycles (15 s at 95° C. plus 1 min at 60° C.). Denaturation curves of 60 to 95° C. (2% slope) were included at the end of the program to verify PCR specificity. Fluorescence was measured during the steps at 60° C. and denaturation in a ABI 7900HT quantitative PCR instrument (Applied Biosystems). In all plates, a negative control and a gene amplification efficiency control curve were included.

Data analysis was performed with the SDS 2.2.1 program (Applied Biosystems). The value of ΔCt was calculated for each sample as $\Delta Ct = Ct - Ct_{ref}$, where Ct is the cycle in which significant amplification was observed and $Ct_{ref}$ is the mean of the Ct values obtained for the WT RT of the BH10 clone. The relative amounts of cDNA obtained were calculated as $2^{\Delta Ct}$, and the values were expressed as the mean±standard deviation of the three values calculated in each experiment.

Copying Fidelity Assays

Copying fidelity of RTs was determined by mispair extension kinetic assays, all carried out under pre-steady-state conditions in order to determine the ability of the various RTs to extend correctly or incorrectly paired template-primer complexes (Matamoros et al. *J. Mol. Biol.* 2008; 375: 1234-1248; Barrioluengo et al. *Biochem J* 2011; 436: 599-607). In addition, genetic assays were carried out based on the expression of the lacZa gene in the context of the M13mp2 phage (Bebenek and Kunkel. *Methods Enzymol.* 1995; 262: 217-232; Barrioluengo et al. *Biochem J* 2011; 436: 599-607).

The invention claimed is:

1. A polypeptide that codes for a protein with reverse transcriptase activity isolated from HIV-1 group O that has higher stability at high temperatures and has higher activity than the parent enzyme at temperatures exceeding 75° C., maintaining copying fidelity, and characterized in that its amino acid sequence has an identity of at least 80% with the parental sequence SEQ ID NO 1 and in that it comprises at least the following amino acid changes:

replacement of the original amino acid lysine (K) by the amino acid arginine (R) in the position homologous to position 358 of SEQ ID NO 1 (mutation K358R), replacement of the original amino acid alanine (A) by the amino acid glycine (G) in the position homologous to position 359 of SEQ ID NO 1 (mutation A359G), and replacement of the original amino acid serine (S) by the amino acid alanine (A) in the position homologous to position 360 of SEQ ID NO 1 (mutation S360A).

2. A polypeptide of claim 1 wherein the amino acid sequence also has one of the following additional mutations or any combination of them:

a) Replacement of the original amino acid threonine (T) by the insertion of two amino acids serine and one glycine (SSG) in the position homologous to position 69 of SEQ ID NO 1 (mutation T69SSG), b) Replacement of the original amino acid threonine (T) by the amino acid alanine (A) in the position homologous to position 355 of SEQ ID NO 1 (mutation T355A), c) Replacement of the original amino acid glutamine (Q) by the amino acid methionine (M) in the position homologous to position 357 of SEQ ID NO 1 (mutation Q357M), and d) Replacement of the original amino acid glutamic acid (E) by the amino acid glutamine (Q) in the position homologous to position 478 of SEQ ID NO 1 (E478Q).

3. A polypeptide of claim 1 characterized in that its sequence corresponds to SEQ ID NO 3.

4. A polypeptide of claim 2 characterized in that its sequence corresponds to SEQ ID NO 5.

5. A polypeptide of claim 2 characterized in that its sequence corresponds to SEQ ID NO 7.

6. A polypeptide of claim 2 characterized in that its sequence corresponds to SEQ ID NO 9.

7. A polypeptide of claim 1 that additionally has MNS flanking sequences at the N-terminal end and a histidine tail at the C-terminal end, characterized in that its sequence corresponds to any of the following: SEQ ID NO 13, SEQ ID NO 15, SEQ ID NO 17, SEQ ID NO 19.

8. A polynucleotide that codes for a polypeptide with reverse transcriptase activity isolated from HIV-1 group O that has higher stability at high temperatures and has higher activity than the parent enzyme at temperatures exceeding 75° C., maintaining copy fidelity, characterized in that it codes for the nucleotide sequences of claim 1.

9. A polynucleotide of claim 8 characterized in that its sequence corresponds to any of the following: SEQ ID NO 4, SEQ ID NO 6, SEQ ID NO 8, SEQ ID NO 10, SEQ ID NO 14, SEQ ID NO 16, SEQ ID NO 18, SEQ ID NO 20.

10. A vector characterized in that it comprises the polynucleotide of claim 8.

11. A host cell comprising the polynucleotide of claim 8 characterized in that it is a bacterium.

12. A host cell of claim 11 characterized in that it is *Escherichia coli*.

13. A method for obtaining a polypeptide characterized in that it comprises the following steps:
    a) introducing a vector of claim 10 in a suitable host cell,
    b) culturing the host cell in a suitable medium, and
    c) purifying the polypeptide with reverse transcriptase activity.

14. A method of reverse transcription of a template nucleic acid that comprises:
    a) mixing the template nucleic acid with the polypeptide of claim 1,
    b) incubating the mixture of step (a) in conditions that enable the synthesis of DNA that is complementary to the template nucleic acid.

15. A method of amplification of a template nucleic acid that comprises:
    a) mixing the nucleic acid with the polypeptide of claim 1 and with at least one DNA-dependent DNA polymerase, and
    b) incubating the mixture of step (a) in conditions that enable the amplification of the DNA complementary to the template nucleic acid.

16. A method of sequencing a nucleic acid that comprises:
    a) putting the nucleic acid in contact with the polypeptide of claim 1,
    b) incubating this mixture in conditions that enable the synthesis of a population of DNA molecules that are complementary to the template nucleic acid, and
    c) separating this population of molecules of complementary DNA to determine the nucleotide sequence.

17. A kit comprising components for carrying out a method of reverse transcription of a template nucleic acid, amplification of a template nucleic acid, or sequencing a nucleic acid, the kit comprising:
    a) the polypeptide of claim 1, and
    b) at least one component of the list comprising:
        i) a buffer,
        ii) a primer,
        iii) a DNA-dependent DNA polymerase, and
        iv) a nucleotide.

18. A host cell characterized in that it comprises the polynucleotide of claim 8 and is capable of producing the polypeptide that codes for a protein with reverse transcriptase activity isolated from HIV-1 group O that has higher stability at high temperatures and has higher activity than the parent enzyme at temperatures exceeding 75° C., maintaining copy fidelity, and characterized in that its amino acid sequence has an identity of at least 80% with the parental sequence SEQ ID NO 1 and in that it comprises at least the following amino acid changes:
    replacement of the original amino acid lysine (K) by the amino acid arginine (R) in the position homologous to position 358 of SEQ ID NO 1 (mutation K358R),
    replacement of the original amino acid alanine (A) by the amino acid glycine (G) in the position homologous to position 359 of SEQ ID NO 1 (mutation A359G), and
    replacement of the original amino acid serine (S) by the amino acid alanine (A) in the position homologous to position 360 of SEQ ID NO 1 (mutation S360A).

19. A host cell characterized in that it comprises the vector of claim 10 and is capable of producing the polypeptide that codes for a protein with reverse transcriptase activity isolated from HIV-1 group O that has higher stability at high temperatures and has higher activity than the parent enzyme at temperatures exceeding 75° C., maintaining copy fidelity, and characterized in that its amino acid sequence has an identity of at least 80% with the parental sequence SEQ ID NO 1 and in that it comprises at least the following amino acid changes:
    replacement of the original amino acid lysine (K) by the amino acid arginine (R) in the position homologous to position 358 of SEQ ID NO 1 (mutation K358R),
    replacement of the original amino acid alanine (A) by the amino acid glycine (G) in the position homologous to position 359 of SEQ ID NO 1 (mutation A359G), and
    replacement of the original amino acid serine (S) by the amino acid alanine (A) in the position homologous to position 360 of SEQ ID NO 1 (mutation S360A).

* * * * *